(12) United States Patent
Skorheim et al.

(10) Patent No.: US 10,796,596 B2
(45) Date of Patent: *Oct. 6, 2020

(54) CLOSED-LOOP INTERVENTION CONTROL SYSTEM

(71) Applicant: HRL Laboratories, LLC, Malibu, CA (US)

(72) Inventors: Steven W. Skorheim, Canoga Park, CA (US); Michael D. Howard, Westlake Village, CA (US); Praveen K. Pilly, West Hills, CA (US)

(73) Assignee: HRL Laboratories, LLC, Malibu, CA (US)

(*) Notice: Subject to any disclaimer, the term of this patent is extended or adjusted under 35 U.S.C. 154(b) by 18 days.

This patent is subject to a terminal disclaimer.

(21) Appl. No.: 15/798,325

(22) Filed: Oct. 30, 2017

(65) Prior Publication Data

US 2018/0068581 A1 Mar. 8, 2018

Related U.S. Application Data

(63) Continuation-in-part of application No. 15/682,065, filed on Aug. 21, 2017, and a continuation-in-part of
(Continued)

(51) Int. Cl.
*A61N 1/36* (2006.01)
*G09B 19/00* (2006.01)
(Continued)

(52) U.S. Cl.
CPC ............ *G09B 19/00* (2013.01); *A61B 5/0476* (2013.01); *A61B 5/165* (2013.01); *A61B 5/4812* (2013.01);
(Continued)

(58) Field of Classification Search
CPC ................................................ A61N 1/36025
See application file for complete search history.

(56) References Cited

U.S. PATENT DOCUMENTS 5,722,418 A 3/1998 Bro
8,073,540 B2 12/2011 Noren
(Continued)

FOREIGN PATENT DOCUMENTS

KR 10-2016-0081454 7/2016
WO WO 03-067555 8/2003

OTHER PUBLICATIONS

Reiner, Miriam et al. "Better than sleep: Theta neurofeedback training accelerates memory consolidation". Biological Psychology 95 (2014) 45-53. (Year: 2014).*

(Continued)

*Primary Examiner* — Allen Porter
(74) *Attorney, Agent, or Firm* — Tope-McKay & Associates

(57) ABSTRACT

Described is a closed-loop intervention control system for memory consolidation in a subject. During operation, the system simulates memory changes of a first memory in a subject during waking encoding of the memory, and then while the subject is sleeping and coupled to an intervention system. Based on the simulated memory changes, the system predicts behavioral performance for the first memory, the behavioral performance being a probability that the first memory can be recalled on cue. The system can be used to control operation (e.g., turn on or off) of the intervention system with respect to the first memory based on the behavioral performance of the first memory determined by the simulation.

21 Claims, 9 Drawing Sheets

Related U.S. Application Data application No. 15/332,787, filed on Oct. 24, 2016, and a continuation-in-part of application No. 15/227,922, filed on Aug. 3, 2016, now Pat. No. 10,092,753.

(60) Provisional application No. 62/516,457, filed on Jun. 7, 2017, provisional application No. 62/440,820, filed on Dec. 30, 2016, provisional application No. 62/410,533, filed on Oct. 20, 2016, provisional application No. 62/247,435, filed on Oct. 28, 2015, provisional application No. 62/245,730, filed on Oct. 23, 2015, provisional application No. 62/210,890, filed on Aug. 27, 2015, provisional application No. 62/210,907, filed on Aug. 27, 2015.

(51) Int. Cl.
| | |
|---|---|
| G05B 19/048 | (2006.01) |
| G05B 17/02 | (2006.01) |
| A61B 5/0476 | (2006.01) |
| A61B 5/16 | (2006.01) |
| A61M 21/00 | (2006.01) |
| A61B 5/00 | (2006.01) |
| A61M 21/02 | (2006.01) |
| G06Q 10/06 | (2012.01) |
| A61B 5/0488 | (2006.01) |
| A61B 5/0402 | (2006.01) |
| G05B 13/02 | (2006.01) |

(52) U.S. Cl.
CPC .......... *A61B 5/4836* (2013.01); *A61M 21/00* (2013.01); *A61M 21/02* (2013.01); *A61N 1/36025* (2013.01); *G05B 17/02* (2013.01); *G05B 19/048* (2013.01); *A61B 5/0402* (2013.01); *A61B 5/0488* (2013.01); *A61B 5/486* (2013.01); *A61B 5/7275* (2013.01); *A61M 2021/0016* (2013.01); *A61M 2021/0027* (2013.01); *A61M 2021/0072* (2013.01); *A61M 2205/502* (2013.01); *A61M 2230/04* (2013.01); *A61M 2230/10* (2013.01); *A61M 2230/18* (2013.01); *A61M 2230/60* (2013.01); *G05B 13/0265* (2013.01); *G05B 2219/23026* (2013.01); *G06Q 10/06398* (2013.01)

(56) References Cited

U.S. PATENT DOCUMENTS

| | | | |
|---|---|---|---|
| 8,718,778 | B2 | 5/2014 | Bikson et al. |
| 9,043,993 | B1* | 6/2015 | James ................. A01K 15/021 |
| 9,116,835 | B1 | 8/2015 | Smyth |
| 9,370,658 | B2 | 6/2016 | Neuvonen |
| 10,067,516 | B2 | 9/2018 | Ramagem |
| 2009/0105785 | A1* | 4/2009 | Wei ................... A61N 1/36132 607/48 |
| 2009/0319002 | A1 | 12/2009 | Simon |
| 2012/0046531 | A1 | 2/2012 | Hua |
| 2012/0245653 | A1 | 9/2012 | Bikson et al. |
| 2012/0251989 | A1 | 10/2012 | Wetmore et al. |
| 2012/0265261 | A1 | 10/2012 | Bikson |
| 2013/0341090 | A1 | 12/2013 | Zeinddine et al. |
| 2014/0051045 | A1 | 2/2014 | Stults et al. |
| 2014/0057232 | A1 | 2/2014 | Wetmore |
| 2014/0275838 | A1 | 9/2014 | Osorio |
| 2015/0025590 | A1 | 1/2015 | Cheng |
| 2015/0240620 | A1 | 8/2015 | Bang et al. |
| 2015/0337647 | A1 | 11/2015 | Kostov et al. |
| 2016/0004224 | A1 | 1/2016 | Pi |
| 2016/0063397 | A1 | 3/2016 | Ylipaavalniemi |
| 2016/0175589 | A1 | 6/2016 | Wingeier |
| 2016/0228702 | A1 | 8/2016 | Kempe |
| 2016/0245070 | A1 | 8/2016 | Vansteenwyk |
| 2016/0281489 | A1 | 9/2016 | Dykstra et al. |
| 2016/0361020 | A1 | 12/2016 | LeBoeuf |
| 2018/0160912 | A1 | 6/2018 | Martin |

OTHER PUBLICATIONS

Dandamudi, S.P. "Introduction to Assembly Language Porgramming for Pentium and RSIC Processors." 2005, XXIV, 692p., Hardcover. Ch. 2 pp. 19-44. (Year: 2005).*

Anderson, J. R., Bothell, D., Byrne, M. D., Douglass, S., Lebiere, C., & Qin. Y. An integrated theory of the mind, (ACT-R), Psychological Review 111, (4), 2004, pp. 1036-1060.

McNamara CG, Tejero-Cantero A, Trouche S, Campo-Urriza N, Dupret D. Dopaminergic neurons promote hippocampal reactivation and spatial memory persistence. Nat Neurosci. 2014;17: pp. 1658-1660.

Marshall L, Helgadóttir H, Mölle M, Born J. Boosting slow oscillations during sleep potentiates memory. Nature. 2006;444: pp. 610-613.

Javadi AH, Walsh V. Transcranial direct current stimulation (tDCS) of the left dorsolateral prefrontal cortex modulates declarative memory. Brain Stimulat. 2012;5: pp. 231-241.

Rasch B, Büchel C, Gais S, Born J. Odor cues during slow-wave sleep prompt declarative memory consolidation. Science. 2007;315: pp. 1426-1429.

Rudoy JD, Voss JL, Westerberg CE, Paller KA. Strengthening Individual Memories by Reactivating Them During Sleep. Science. 2009;326: p. 1079.

Bendor D, Wilson MA. Biasing the content of hippocampal replay during sleep. Nat. Neurosci. 2012;15: pp. 1439-1444.

Euston DR, Gruber AJ, McNaughton BL. The role of medial prefrontal cortex in memory and decision making. Neuron. 2012;76: pp. 1057-1070.

Ji D, Wilson MA. Coordinated memory replay in the visual cortex and hippocampus during sleep. Nat. Neurosci. 2007;10: pp. 100-107.

Abeyratne UR, Swarnkar V, Rathnayake SI, Hukins C. Sleep-stage and event dependency of brain asynchrony as manifested through surface EEG. Conf. Proc. Annu. Int. Conf. IEEE Eng. Med. Biol. Soc. IEEE Eng. Med. Biol. Soc. Conf. 2007;2007: pp. 709-712.

Salmi T, Brander PE. Computer assisted detection of REM and non-REM sleep for analysis of nocturnal hypoxaemia in patients with ventilatory impairment. Int. J. Clin. Monit. Comput. 1994;11: pp. 63-70.

Euston et al. Fast-Forward Playback of Recent Memory Sequences in Prefrontal Cortex During Sleep. Science. Nov. 2007; 318 (5853): pp. 1147-1150.

The SenseWear armband as a Sleep Detection Device [Internet]. [cited Nov. 23, 2014]. pp. 1-9. Available from: http://www.bodymedia. com/Professionals/Whitepapers/The-SenseWear-armband-as-a-Sleep-Detection-Device?whence=.

Ruffini et al., Optimization of multifocal transcranial current stimulation for weighted cortical pattern targeting from realistic modeling of electric fields, Neuroimage, 89:216-25, 2014.

Rissman and Wagner, "Distributed Representations in Memory: Insights from Functional Brain Imaging," Annual Rev Psychol, 63: 101-128, 2012.

Rolls, "The Mechanisms for Pattern Completion and Pattern Separation in the Hippocampus," Frontiers in Systems Neuroscience, 7: 74, 2013.

McHugh et al, "Dentate Gyrus NMDA Receptors Mediate Rapid Pattern Separation in the Hippocampal Network," Science, 317(5834): 94-99, 2007.

Michael Schirner, et al., "An automated pipeline for constructing personalized virtual brians from multimodal neuroimaging data," NeuroImage, vol. 117, Aug. 15, 2015, pp. 343-357.

Krause, M. R., Zanos, T. P., Csorba, B. A., Pilly, P. K., Choe, J., Phillips, M. E., Data, A., and Pack, C. C. (2017). Transcranial direct current stimulation facilitates associative learning and alters functional connectivity in the primate brain. Current Biology, 27(3), pp. 3086-3096.

Office Action 1 for U.S. Appl. No. 15/227,922, dated Dec. 13, 2016.

(56) References Cited

OTHER PUBLICATIONS

Tremblay, Sara, et al. "The Uncertain Outcome of Prefrontal TDCS." Brain Stimulation 7.6 (2014): 773-83. Web.

Segrace, R.A. et al. "Concurrent Cognitive Control Training Augments the Antidepressant Efficacy of TDCS: A Pilot Study." Brain Stimulation 7.2 (2014): 325-31. Web.

Castano-Candamil, Ssebastian et al. "Solving the EEG Inverse Problem Based on Space-Time-Frequency Structured Sparsity Constraints." Neuroimage 118 (2015) 598-612. Web.

Marshall, L. "Transcranial Direct Current Stimulation during Sleep Improves Declarative Memory." Journal of Neuroscience 24.44 (2004): 9985-992. Web.

Javadi, Amir Homayoun, and Paul Cheng. "Transcranial Direct Current Stimulation (tDCS) Enhances Reconsolidation of Long-Term Memory." Brain Stimulation 6.4 (2013): 668-74. Web.

Sahlem, Gregory L., et al. "Oscillating Square Wave Transcranial Direct Current Stimulation (tDCS) Delivered During Slow Wave Sleep Does Not Improve Declarative Memory More Than Sham: A Randomized Sham Controlled Crossover Study." Brain Stimulation 8.3 (2015): 528-34. Web.

Barham, Michael P., Peter G. Enticott, Russell Conduit, and Jarrad A.g. Lum. "Transcranial Electrical Stimulation during Sleep Enhances Declarative (but Not Procedural) Memory Consolidation: Evidence from a Meta-analysis." Neuroscience & Biobehavioral Reviews 63 (2016): 65-77. Web.

Eggert, Torsten, Hans Dorn, Cornelia Sauter, Michael A. Nitsche, Malek Bajbouj, and Heidi Danker-Hopfe. "No Effects of Slow Oscillatory Transcranial Direct Current Stimulation (tDCS) on Sleep-Dependent Memory Consolidation in Healthy Elderly Subjects." Brain Stimulation 6.6 (2013): 938-45. Web.

Westerberg, Carmen E., Susan M. Florczak, Sandra Weintraub, M. -Marsel Mesulam, Lisa Marshall, Phyllis C. Zee, and Ken A. Paller. "Memory Improvement via Slow-oscillatory Stimulation during Sleep in Older Adults." Neurobiology of Aging 36.9 (2015): 2577-586. Web.

Response to Office Action 1 for U.S. Appl. No. 15/227,922, dated Mar. 13, 2017.

Office Action 2 for U.S. Appl. No. 15/227,922, dated Apr. 24, 2017.
Response to Office Action 2 for U.S. Appl. No. 15/227,922, dated Aug. 24, 2017.

Office Action 3 for U.S. Appl. No. 15/227,922, dated Sep. 29, 2017.
Response to Office Action 3 for U.S. Appl. No. 15/227,922, dated Jan. 29, 2018.

Rudoy JD, Voss JL, Westerberg CE, Paller KA. Strengthening Individual Memories by Reactivating Them During Sleep. Science. 2009; 326: pp. 1079-1079.

Diekelmann S, Biggel S, Rasch B, Born J. Offline consolidation of memory varies with time in slow wave sleep and can be accelerated by cuing memory reactivations. Neurobiol. Learn. Mem. 2012; 98: pp. 103-111.

Kato Y, Endo H, Kizuka T. Mental fatigue and impaired response processes: event-related brain potentials in a Go/ NoGo task. Int. J. Psychophysiol. Off. J. Int. Organ. Psychophysiol. 2009; 72: pp. 204-211.

Henckens MJAG, Hermans EJ, Pu Z, Joëls M, Fernández G. Stressed Memories: How Acute Stress Affects Memory Formation in Humans. J. Neurosci. 2009; 29: pp. 10111-10119.

Akin M, Kurt MB, Sezgin N, Bayram M. Estimating vigilance level by using EEG and EMG signals. Neural Comput. Appl. 2007; 17: pp. 227-236.

Jaar O, Pilon M, Carrier J, Montplaisir J, Zadra A. Analysis of Slow-Wave Activity and Slow-Wave Oscillations Prior to Somnambulism. Sleep. 2010; 33: pp. 1511-1516.

Itti L, Koch C. A saliency-based search mechanism for overt and covert shifts of visual attention. Vision Res. 2000; 40: pp. 1489-1506.

Botteldooren D, DeCoensel B. The role of saliency, attentio n and source identification in soundscape research. ProcInternoise 2009 [Internet]. Ottowa, Canada; 2009, pp. 1-9, Available from http://citeseerx.ist.psu.edu/viewdoc/download?doi=10.1.1.468.8119&rep=rep1&type=pdf.

Lebiere C, Pirolli P, Thomson R, Paik J, Rutledge-Taylor M, Staszewski J, et al. A Functional Model of Sensemaking in a Neurocognitive Architecture. Comput. Intell. Neurosci. [Internet]. vol. 2013, pp. 1-29, Article ID 921695. Available from: http://www.hindawi.com/journals/cin/2013/921695/abs/.

Notification of Transmittal of International Search Report and the Written Opinion of the International Searching Authority for PCT/US2017/047865; dated Nov. 27, 2017.

International Search Report of the International Searching Authority for PCT/US2017/047865; dated Nov. 27, 2017.

Written Opinion of the International Searching Authority for PCT/US2017/047865; dated Nov. 27, 2017.

Alex Lilijecrantz, "Memory Consolidation in Artificial Neural Networks," 2 003, https://www.nada.kth.se/utbildning/grukth/exjobb/rapportlistor/2003/rapporter03/liljencrantz_axel_03148.pdf, see pp. 6-7.

Marshall L, Helgadóttir H, Mölle M, Born J. Boosting slow oscillations during sleep potentiates memory. Nature. 2006; 444(7119): pp. 610-613.

Rudoy JD, Voss JL, Westerberg CE, Paller KA. Strengthening Individual Memories by Reactivating Them During Sleep. Science. Nov. 20, 2009;326(5956): pp. 1079-1079.

Diekelmann S, Biggel S, Rasch B, Born J. Offline consolidation of memory varies with time in slow wave sleep and can be accelerated by cuing memory reactivations. Neurobiol Learn Mem. Sep. 2012; 98(2): pp. 103-111.

Rasch BH, Born J, Gais S. Combined blockade of cholinergic receptors shifts the brain from stimulus encoding to memory consolidation. J Cogn Neurosci. May 2006; 18(5): pp. 793-802.

Gais S, Born J. Low acetylcholine during slow-wave sleep is critical for declarative memory consolidation. Proc Natl Acad Sci U S A. Feb. 17, 2004; 101(7): pp. 2140-2144.

Rasch B, Buchel C, Gais S, Born J. Odor cues during slow-wave sleep prompt declarative memory consolidation. Science. 2007; 315(5817): pp. 1426-1429.

Kirov R, Weiss C, Siebner HR, Born J, Marshall L. Slow oscillation electrical brain stimulation during waking promotes EEG theta activity and memory encoding. Proc. Natl. Acad. Sci. 2009;106: pp. 15460-15465.

Jutras MJ, Fries P, Buffalo EA. Oscillatory activity in the monkey hippocampus during visual exploration and memory formation. Proc Natl Acad Sci. Aug. 6, 2013; 110(32): pp. 13144-13149.

Brincat SL, Miller EK. Frequency-specific hippocampal-prefrontal interactions during associative learning. Nat Neurosci Apr. 2015; 18(4): pp. 576-581.

McNamara CG, Tejero-Cantero A, Trouche S, Campo-Urriza N, Dupret D. Dopaminergic neurons promote hippocampal reactivation and spatial memory persistence. Nat Neurosci. 2014 12//print; 17(12): pp. 1658-1660.

Ji D, Wilson MA. Coordinated memory replay in the visual cortex and hippocampus during sleep. Nat Neurosci. 2007; 10(1): pp. 100-107.

Kali S, Dayan P. Off-line replay maintains declarative memories in a model of hippocampal-neocortical interactions. Nat Neurosci. 2004; 7(3): pp. 286-294.

Rolls ET. Hippocampo-cortical and cortico-cortical backprojections. Hippocampus. 2000; 10: pp. 380-388.

Creutzfeldt OD, Fromm GH, Kapp H. Influence of transcortical d-c currents on cortical neuronal activity. Exp Neurol. Jun. 1962; 5: pp. 436-452.

Sederberg PB, Kahana MJ, Howard MW, Donner EJ, Madsen JR. Theta and gamma oscillations during encoding predict subsequent recall. J Neurosci Off J Soc Neurosci. Nov. 26, 2003; 23(34): pp. 10809-10814.

Osipova D, Takashima A, Oostenveld R, Fernandez G, Maris E, Jensen O. Theta and gamma oscillations predict encoding and retrieval of declarative memory. J Neurosci. 2006; 26(28): pp. 7523-7531.

(56) References Cited

OTHER PUBLICATIONS

Fröhlich F, McCormick DA. Endogenous electric fields may guide neocortical network activity. Neuron. Jul. 15, 2010; 67(1): pp. 129-143.
Ngo, H. V. V., Martinetz, T., Born, J., & Mölle, M. (2013). Auditory closed-loop stimulation of the sleep slow oscillation enhances memory. Neuron, 78(3), pp. 545-553.
Braboszcz, C. et al., "Lost in thoughts: Neural markers of low alertness during mind wandering" NeuroImage, 54(4), pp. 3040-3047 (2011).
Trejo, L. J. et al., "EEG-Based Estimation and Classification of Mental Fatigue" Psychology, 06(05), pp. 572-589 (2015).
Healey, J. A. et al. "Detecting stress during real-world driving tasks using physiological sensors" IEEE Transactions on Intelligent Transportation Systems, 6(2), pp. 156-166 (2005).
Oweis, R. et al. "QRS Detection and Heart Rate Variability Analysis: A Survey" Biomedical Science and Engineering, 2, pp. 13-34. 10.12691/bse-2-1-3 (2014).
Rodgers, J. L. et al. "Thirteen ways to look at the correlation coefficient" The American Statistician. 42 (1): pp. 59-66 (1988).
Erden, F. et al. "Contact-free measurement of respiratory rate using infrared and vibration sensors" Infrared Physics & Technology. Nov. 1, 2015;73:pp. 88-94 (2015).
Procházka, A. "Microsoft kinect visual and depth sensors for breathing and heart rate analysis" Sensors. Jun. 28, 2016;16(7):996 (2016), pp. 1-11.
Nelder, J. et al. "Generalized Linear Models" Journal of the Royal Statistical Society. Series A (General). Blackwell Publishing. 135 (3): pp. 370-384 (1972).
Delorme, A. et al. "Eeglab: an open source toolbox for analysis of single-trial eeg dynamics including independent component analysis" Journal of neuroscience methods 134, pp. 9-21 (2004).
Daly, I. et al. "On the automated removal of artifacts related to head movement from the eeg" IEEE Transactions on neural systems and rehabilitation engineering 21, pp. 427-434 (2013).
Daly, I. et al. "What does clean eeg look like?" In Engineering in Medicine and Biology Society (EMBC), 2012 Annual International Conference of the IEEE (IEEE), pp. 3963-3966.
Herwig, U. et al. "Using the international 10-20 EEG system for positioning of transcranial magnetic stimulation" Brain topography. Dec. 1, 2003;16(2):pp. 95-99.
T. VanderPlas, J. "Understanding the Lomb-Scargle Periodogram" arXiv:1703.09824 [astro-ph.IM] (2017), pp. 1-55.
Nakagawa, S. et al. "A general and simple method for obtaining R2 from generalized linear mixed-effects models" Methods in Ecology and Evolution. Feb. 1, 2013;4(2): pp. 133-142.
Fisher, R. A. "The Use of Multiple Measurements in Taxonomic Problems" Annals of Eugenics. 7 (2): pp. 179-188 (1936).
Cortes, C. "Support-vector networks" Machine Learning. 20 (3): pp. 273-297 (1995).
Ben-Hur, A. "Support vector clustering" Journal of Machine Learning Research, 2: pp. 125-137 (2001).
Drucker, H. "Support Vector Regression Machines" Advances in Neural Information Processing Systems 9, NIPS 1996, pp. 155-161, MIT Press (1997).
Notification of Transmittal of International Search Report and the Written Opinion of the International Searching Authority for PCT/US2017/063544; dated Mar. 16, 2018.
International Search Report of the International Searching Authority for PCT/US2017/063544; dated Mar. 16, 2018.
Written Opinion of the International Searching Authority for PCT/US2017/063544; dated Mar. 16, 2018.
Nader K, Schafe GE, Le Doux JE. Fear memories require protein synthesis in the amygdala for reconsolidation after retrieval. Nature. 2000; 406: pp. 722-726.
Dudai Y. The neurobiology of consolidations, or, how stable is the engram? Annu. Rev. Psychol. 2004; 55: pp. 51-86.
Squire LR, Alvarez P. Retrograde amnesia and memory consolidation: a neurobiological perspective. Curr. Opin. Neurobiol. 1995; 5: pp. 169-177.
Foa EB. Social anxiety disorder treatments: psychosocial therapies. J. Clin. Psychiatry. 2006; 67 Suppl 12: pp. 27-30.
Seidler GH, Wagner FE. Comparing the efficacy of EMDR and trauma-focused cognitive-behavioral therapy in the treatment of PTSD: a meta-analytic study. Psychol. Med. 2006; 36: pp. 1515-1522.
Bustos SG, Maldonado H, Molina VA. Midazolam disrupts fear memory reconsolidation. Neuroscience. 2006; 139: pp. 831-842.
Sandrini M, Censor N, Mishoe J, Cohen LG. Causal Role of Prefrontal Cortex in Strengthening of Episodic Memories through Reconsolidation. Curr. Biol. 2013; 23: pp. 2181-2184.
Soterix Medical Website. High Definition-transcranial Direct Current Stimulation (HD-tDCS) [Internet]. Available from: http://soterixmedical.com/hd-tdcs, downloaded Aug. 8, 2016, pp. 1-13.
Chan JCK, LaPaglia JA. Impairing existing declarative memory in humans by disrupting reconsolidation. Proc. Natl. Acad. Sci. 2013;110: pp. 9309-9313.
Brunet A, Orr SP, Tremblay J, Robertson K, Nader K, Pitman RK. Effect of post-retrieval propranolol on psychophysiologic responding during subsequent script-driven traumatic imagery in post-traumatic stress disorder. J. Psychiatr. Res. 2008;42: pp. 503-506.
Wolters CH, Anwander A, Tricoche X, Weinstein D, Koch MA, MacLeod RS. Influence of tissue conductivity anisotropy on EEG/MEG field and return current computation in a realistic head model: a simulation and visualization study using high-resolution finite element modeling. NeuroImage. 2006; 30: pp. 813-826.
Dmochowski JP, Datta A, Bikson M, Su Y, Parra LC. Optimized multi-electrode stimulation increases focality and intensity at target. J. Neural Eng. 2011; 8:pp. 046011-1-046011-16.
Edmund Rolls, "The mechanisms for pattern completion and pattern separation in the hippocampus," Front Syst Neurosci. Oct. 2013; vol. 7: Article 74, pp. 1-21.
Thomas J. McHugh, et al., "Dentate Gyrus NMDA Receptors Mediate Rapid Pattern Separation in the Hippocampal Network," Science, vol. 317, (Jul. 2007); pp. 94-99.
Jesse Rissman, et al., "Distributed representations in memory: Insights from functional brain imaging," Annu Rev Psychol. 2012 ; 63: pp. 101-128.
Giulio Ruffinia, et al., "Optimization of multifocal transcranial current stimulation for weighted cortical pattern targeting from realistic modeling of electric fields," Neuroimage. Apr. 1, 2014; 89: pp. 216-225.
Office Action 1 for U.S. Appl. No. 15/072,353, dated Oct. 19, 2016.
Tremblay, Sara, et al., "The uncertain outcome of prefrontal TDCS," Brain Stimulation 7.6 (2014): pp. 773-783. Web.
Segrave, R.A., et al., "concurrent cognitive control training augments the anidepressant efficacy of TDCS: A pilot study," Brain Stimulation 7.2 (2014): pp. 325-331. Web.
Castano-Candamil, Sebastian, et al., "Solving the EEG inverse problem based on space-time-frequency structured sparsity constraints," Neuroimage 118 (2015), pp. 598-612. Web.
Response to Office Action 1 for U.S. Appl. No. 15/072,353, dated Feb. 17, 2017.
Office Action 2 for U.S. Appl. No. 15/072,353, dated Apr. 24, 2017.
"An automated pipeline for constructing personalized virtual brains from multimodal neuroimaging data," NeuroImage, vol. 117, Aug. 15, 2015, pp. 343-357.
Krause, M. R., Zanos, T. P., Csorba, B. A., Pilly, P. K., Choe, J., Phillips, M. E., Datta, A., and Pack, C. C. (2017), Transcraning direct current stimulation facilitates associative learning and alters functional coonectivity in the primate brain. Current Biology, 27(3), pp. 3086-3096.
Response to Office Action 2 for U.S. Appl. No. 15/072,353, dated Aug. 22, 2017.
Office Action 3 for U.S. Appl. No. 15/072,353, dated Oct. 6, 2017.
Response to Office Action 3 for U.S. Appl. No. 15/072,353, dated Jan. 8, 2018.
Notice of Allowance for U.S. Appl. No. 15/072,353, dated Apr. 17, 2018.
Notice of Allowance for U.S. Appl. No. 15/227,922, dated May 30, 2018.
Grech, R., Cassar, T., Muscat, J., Camilleri, K.P., Fabri, S.G., Zervakis, M., Xanthopoulos, P., Sakkalis, V. and Vanrumste, B.,

(56) References Cited

OTHER PUBLICATIONS

2008. Review on solving the inverse problem in EEG source analysis. Journal of neuroengineering and rehabilitation, 5(1), pp. 1-33.
Tucker DM. Spatial sampling of head electrical fields: the geodesic sensor net. Electroencephalogr. Clin. Neurophysiol, 87: pp. 154-163, 1993.
Michel C., Murray MM. Towards the utilization of EEG as a brain imaging tool, NeuroImage 61 (2012), pp. 371-385.
Wolters CH, Anwander A, Tricoche X, Weinstein D, Koch MA, MacLeod RS. Influence of tissue conductivity anisotropy on EEG/MEG field and return current computation in a realistic head model: a simulation and visualization study using high-resolution finite element modeling. NeuroImage, 30: pp. 813-826, 2006.
Dmochowski JP, Datta A, Bikson M, Su Y, Parra LC. Optimized multi-electrode stimulation increases focality and intensity at target. J. Neural Eng., 8:046011, 2011, pp. 1-16.
Jones DK and Leemans A, "Diffusion Tensor Imaging", Methods in Molecular Biology 711: pp. 127-144, 2011.
Ramírez, Rey R., and Scott Makeig. "Neuroelectromagnetic source imaging of spatiotemporal brain dynamical patterns using frequency-domain independent vector analysis (IVA) and geodesic sparse Bayesian learning (gSBL)." In Proceedings of the 13th Annual Meeting of the Organization for Human Brain Mapping, Chicago, IL. 2007.
Office Action 1 for U.S. Appl. No. 15/338,118, dated May 23, 2018.
Fox, Peter T., et al., "Column-Based Model of Electric Field Excitation of Cerebral Cortex," Human Brain Mapping 22:1-16 (2004).
Response to Office Action 1 for U.S. Appl. No. 15/338,118, dated Aug. 23, 2018.
Office Action 2 for U.S. Appl. No. 15/338,118, dated Nov. 21, 2018.
Response to Office Action 2 for U.S. Appl. No. 15/338,118, dated Feb. 21, 2019.
Notice of Allowance for U.S. Appl. No. 15/338,118, dated Mar. 11, 2019.
Office Action 1 for U.S. Appl. No. 15/332,787, dated Sep. 18, 2018.
Response to Office Action 1 for U.S. Appl. No. 15/332,787, dated Nov. 6, 2018.
Notice of Allowance for U.S. Appl. No. 15/332,787, dated Jan. 17, 2019.
International Preliminary Report on Patentability for PCT/US2017/059125; dated Apr. 26, 2019.
International Preliminary Report on Patentability Chapter II for PCT/US2017/047865; dated Nov. 15, 2018.
Notification of International Preliminary Report on Patentability Chapter I for PCT/US2017/047865; dated May 2, 2019.
International Preliminary Report on Patentability Chapter I for PCT/US2017/047865; dated May 2, 2019.
Office Action 1 for U.S. Appl. No. 15/682,065, dated Aug. 14, 2019.
Office Action 1 for U.S. Appl. No. 15/944,530, dated Oct. 16, 2019.
Response to Office Action 1 for U.S. Appl. No. 15/944,530, dated Jan. 16, 2020.
Communication pursuant to Rules 161(2) and 162 EPC for European Regional Phase Patent Application No. 17887539.9, dated Aug. 6, 2019.
Response to the communication pursuant to Rules 161(2) and 162 EPC for European Regional Phase Patent Application No. 17887539.9, dated Feb. 11, 2020.
Response to Office Action 1 for U.S. Appl. No. 15/682,065, dated Dec. 13, 2019.

\* cited by examiner

CLOSED-LOOP INTERVENTION CONTROL SYSTEM

CROSS-REFERENCE TO RELATED APPLICATIONS

The present application is a Continuation-in-Part application of U.S. Ser. No. 15/682,065, filed Aug. 21, 2017, which is a non-provisional application of U.S. Provisional Application No. 62/410,533, filed on Oct. 20, 2016, the entirety of which are hereby incorporated by reference.

The present application is ALSO a Continuation-in-Part application of U.S. Ser. No. 15/227,922, filed on Aug. 3, 2016, which is a non-provisional application of U.S. Provisional Application No. 62/210,907, filed on Aug. 27, 2015. U.S. Ser. No. 15/227,922 is also a non-provisional application of U.S. Provisional Application No. 62/210,890, filed on Aug. 27, 2015. U.S. Ser. No. 15/227,922 is also a non-provisional application of U.S. Provisional Application No. 62/247,435, filed on Oct. 28, 2015. All of which are incorporated in their entirety herein by reference.

The present application is ALSO a Continuation-in-Part application of U.S. Ser. No. 15/332,787, filed on Oct. 24, 2016, 2016, which is a non-provisional application of U.S. Provisional Application No. 62/245,730, field on Oct. 23, 2015, the entirety of which are hereby incorporated by reference.

The present application is ALSO a non-provisional patent application of U.S. Provisional Application No. 62/440,820, filed on Dec. 30, 2016, the entirety of which is hereby incorporated by reference.

The present application is ALSO a non-provisional patent application of U.S. Provisional Application No. 62/516,457, filed on Jun. 7, 2017, the entirety of which is hereby incorporated by reference.

GOVERNMENT RIGHTS

This invention was made with government support under U.S. Government Contract Number W911NF-16-C-0018, RAM Replay. The government has certain rights in the invention.

BACKGROUND OF INVENTION

(1) Field of Invention

The present invention relates to memory acquisition system and, more particularly, to a cognitive model-based predictive controller for the enhancement of devices used for memory consolidation, learning and skill acquisition in human subjects.

(2) Description of Related Art

In operational tasks (as in many business and educational scenarios), it can be critically important to quickly integrate new information (based on limited exposure) and accurately recall it. To improve such recall, it is important to have an understanding of memory integration and recall processes. For example, it is widely accepted that new memories are first encoded into short-term memory in the human brain's hippocampal region, and then gradually over a period of days, weeks, or months they are consolidated into a slower-learning, more stable, brain region known as cortex in which long term memories are stored. Once information is consolidated into long-term memory it becomes more resistant to decay. This consolidation process involves events called "replays" that occur during a deep stage of sleep called non-rapid-eye-movement sleep or NREM. The theory holds that the more often a memory is replayed, the better a person performs when tested on a behavior dependent on recall of that memory. Although any memory in the short-term store has a chance of being replayed during sleep, there is a higher probability that a specific memory will be replayed if it was related to some emotional content or high immediate reward. Unfortunately, many things that a person needs to learn are boring or tedious, and the reward for learning them may be a long way off.

To address this issue, several techniques have been tested in an attempt to enhance memory integration and recall. For example, in laboratory experiments, auditory or olfactory cues are associated with toy tasks during task performance, and these cues are then used during sleep to trigger replays of that task performance memory.

By way of example, Rudoy et al. reported memory retention rates on object location experiments with audio cues of 97% after 1.5 hours, which can be extrapolated to 4% after 48 hours (see the List of incorporated Literature References, Reference No, 1). In other work, Diekelman et al, reported an 84% retention on object location experiments with odor cues after 1.67 hours, which can be extrapolated to 5% after 10 hours (see Literature Reference No. 2). Further, Marshall et al, reported a 90% retention on paired associates tasks after 10 hours using tDCS cues, but their technique improved every memory; it did not target specific memories.

While promising, none of the aforementioned techniques incorporate a model-based intervention system to simulate the behavior improvement possible based on the treatment given so far, online, allowing a decision of whether the intervention should be continued or should be stopped. The prior art memory intervention techniques were only tested in a laboratory, under supervised sleep conditions. They were never intended for real-world use; only for research on memory consolidation. Nevertheless, whether in the laboratory or in real-world settings, there exists no method to control which memories need to be enhanced, or to stop the intervention for a particular memory when it has been enhanced sufficiently, to allow other memories to consolidate. This need was never obvious because the science to recognize a particular memory being replayed during sleep had not been developed; therefore, memory interventions were only used for general enhancements of all memories.

To provide such control over specific memory enhancement interventions in the laboratory, and to make this into a commercial product that could be used by individuals apart from a supervised laboratory setting, the intervention delivery system must be automated. That is because while the subject is in slow-wave sleep or any other cognitive state when memory replays occur, electroencephalogram (EEG) readings must be analyzed in real time (within the 1 Hz slow-wave oscillation cycle) to decide which memory intervention should be applied in the next cycle, if at all. No human supervisor can make these determinations as fast as an automated system, and without waking up the subject for performance testing.

Thus, a continuing need exists for an automated intervention control system or controller that makes the intervention approaches efficient and effective by assessing the subject's brain state and predicting in real time when to apply the intervention.

SUMMARY OF INVENTION

This disclosure provides a closed-loop intervention control system for memory consolidation in a subject. In various embodiments, the system includes one or more processors and a memory. The memory is, for example, a non-transitory computer-readable medium having executable instructions encoded thereon, such that upon execution of the instructions, the one or more processors perform several operations, such as simulating memory changes of a first memory in a subject during waking encoding of the memos, and then while the subject is sleeping and coupled to an intervention system; based on the simulated memory changes, predicting behavioral performance for the first memory, the behavioral performance being a probability that the first memory can be recalled on cue; and controlling operation of the intervention system with respect to the first memory based on the behavioral performance of the first memory determined by the simulation. Controlling the invention system includes, for example, turning on or off the intervention system to activate electrodes associated with the intervention system.

In another aspect, the simulated memory changes are based on increases in levels of skill in the memory due to training and replays and on biometric data on the subject when the data correlates with the subject's performance of the skill.

In yet another aspect, simulating memory changes includes encoding and consolidation of specific memory.

Further, the specific memory is encoded in a short-term memory store and consolidated in a long-term memory store.

Additionally, consolidating the specific memory in the long-term memory store includes strengthening representations of the specific memory.

In yet another aspect, consolidating the specific memory in the long-term memory store is performed when the subject is in NREM sleep or quiet waking and each positive phase of Slow-Wave oscillation occurs.

Further, the correlation between biometric data and the subject's performance of a skill is updated every in trials based on a rolling mean biometric and rolling mean performance metric.

In yet another aspect, the system performs an operation of identifying replays of the specific memory and providing an associated quality, the quality being the likelihood that the specific memory was activated at a certain time. The quality is based on recency and frequency of practice of the specific memory.

Finally, the present invention also includes a computer program product and a computer implemented method. The computer program product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

Figure 1:
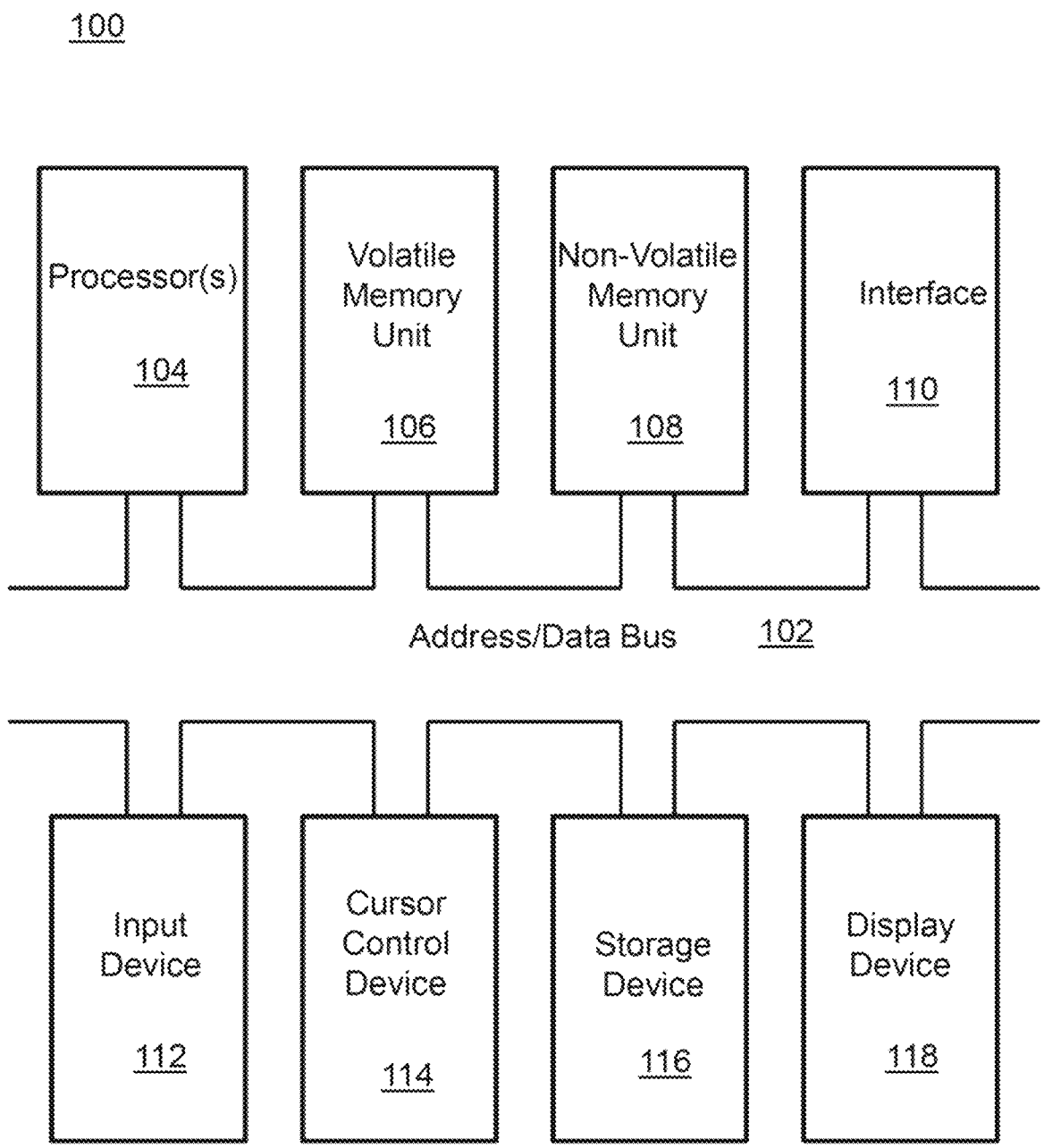
FIG. 1 is a block diagram depicting the components of a system according to various embodiments of the present invention.

The present invention relates to memory acquisition system and, more particularly, to a cognitive model-based predictive controller for the enhancement of devices used for memory consolidation, learning and skill acquisition in human subjects. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a list of cited references is provided. Next, a description of the various principal aspects of the present invention is provided. Subsequently, an introduction provides the reader with a general understanding of the present invention. Finally, specific details of various embodiment of the present invention are provided to give an understanding of the specific aspects.

(1) LIST OF CITED LITERATURE REFERENCES

The following references are cited throughout this application. For clarity and convenience, the references are listed herein as a central resource for the reader. The following references are hereby incorporated by reference as though fully set forth herein. The references are cited in the application by referring to the corresponding literature reference number, as follows:

1. Rudoy J. D., Voss J. L., Westerberg C. E., Paller K. A. Strengthening Individual Memories by Reactivating Them During Sleep. Science. 2009; 326:1079-1079.
2. Diekelmann S, Biggel S, Rasch B, Born J. Offline consolidation of memory varies with time in slow wave sleep and can be accelerated by cuing memory reactivations. Neurobiol. Learn. Mem. 2012; 98:103-111.
3. Marshall L, Helgadóttir H, Mölle Born J. Boosting slow oscillations during sleep potentiates memory. Nature. 2006; 444:610-613.
4. Jaar O, Pilon M, Carrier J, Montplaisir J, Zadra A. Analysis of Slow-Wave Activity and Slow-Wave Oscillations Prior to Somnambulism. Sleep. 2010; 33:1511-1516.
5. Anderson, J. R., Bothell, D., Byrne, M. D., Douglass, S., Lebiere, C., & Qin. Y. An integrated theory of the mind," (ACT-R), Psychological Review 111, (4), 2004, 1036-1060.

(2) PRINCIPAL ASPECTS

Various embodiments of the invention include three "principal" aspects. The first is an intervention control system (controller) for the enhancement of memory consolidation, learning and skill acquisition in human subjects. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured, to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, application-specific integrated circuit (ASIC), programmable logic array (PLA), complex programmable logic device (CPLD), or a field programmable gate array (FPGA).

The computer system 100 is configured to utilize one or more data storage units. The computer system 100 may include a volatile memory unit 106 (e.g., random access memory ("RAM"), static RAM, dynamic. RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline serial cables, modems, network adaptors, etc.) and/or wireless (e.g., wireless modems, wireless network adaptors, etc) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include, alphanumeric and/or function keys. Alternatively, the input device 112 may be an input device other than an alphanumeric input device. In an aspect, the computer system. 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer, in one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
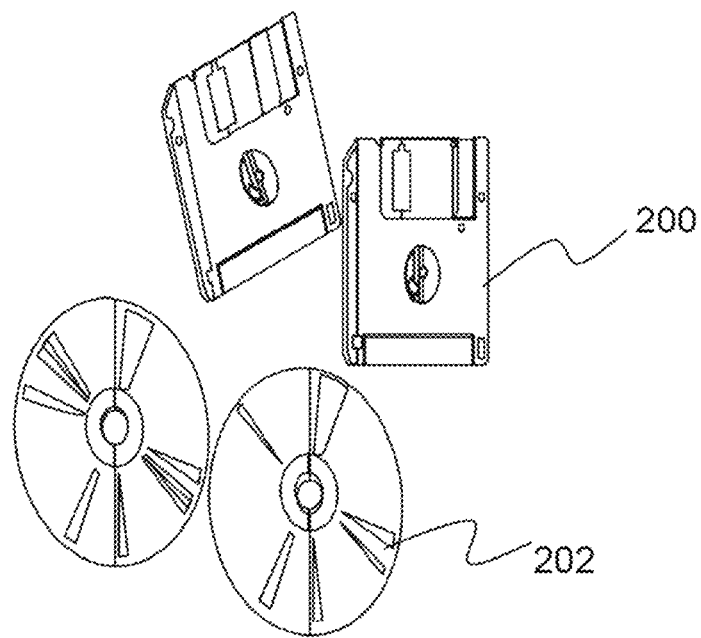
FIG. 2 is an illustration of a computer program product embodying an aspect of the present invention.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) INTRODUCTION

This disclosure provides a cognitive model-based predictive controller (or otherwise referred to as a "intervention control system") that is a useful addition to improve the efficacy and efficiency of interventions used to improve consolidation of specific memories; e.g., memories of specific things that must be learned quickly and remembered clearly and easily. There are several prior art interventions (listed below) that can be improved upon by adding the intervention control system of this disclosure.

The intervention control system described herein provides a fast yet sufficiently expressive model of the way that humans learn new memories and skills, in terms of how the representations in the brain are initially encoded into volatile short-term memory, and then gradually get consolidated into more stable and persistent long-term memory. The model of this disclosure supplements the closed-loop model-based control system (as disclosed in U.S. Ser. No. 15/682,065) and, in doing so, provides a useful addition to improve the efficacy of interventions used, to improve consolidation of specific memories (e.g., memories of specific things that must be learned quickly and remembered clearly and easily).

The model of this disclosure simulates (at a functional level) the encoding and consolidation of memories, and makes predictions of the resulting behavioral performance (i.e., the subsequent ability to recall and use memories of interest). Used in a control loop with brain sensors and the intervention system, this model turns on the intervention when the behavioral predictions are below a desired level, and turns it off when behavioral predictions surpass a threshold of performance. Since there are many memories that need to be consolidated during the night, an intervention to improve one specific memory must not prevent consolidation of other memories; an issue addressed by the model-based predictive controller of the present invention. Importantly, the model updates its representations and makes new predictions very quickly and efficiently, which is its advantage over previously described systems and models.

Such an intervention control system for a memory improvement intervention, using behavioral performance predictions to decide when interventions are needed during sleep, has never been conceived of before. In operational tasks (as in many business and educational scenarios), it can be critically important to quickly integrate new information (based on limited exposure) and accurately recall it. A purpose of the invention is to control interventions that enhance memory consolidation, to make this possible. Although it is widely accepted that memories are consolidated during sleep, and a few prior art laboratory experiments have implemented some targeted interventions; the invention described herein is the first to implement a control loop around an intervention, to control exactly when an intervention should be applied in order to achieve the desired level of performance. The intervention control system will automatically determine when and if certain interventions should be applied during sleep and quiet waking periods. It does this by predicting behavioral performance outcomes resulting from memory replay activity in real-time during quiet waking or slow wave sleep, thereby allowing selection of the best replay intervention options to achieve a desired performance. When the predicted performance reaches the desired level, the model turns off the interventions, allowing other memories to be consolidated.

The model is shaped by the sequence and content of all experienced stimuli in a situation paradigm, as well as the characteristics of prior replay events, so it can predict the impact that further intervention will have on behavior. Without the intervention control system, the interventions during sleep to improve consolidation of a specific memory or memories are typically uninformed. Conventional systems typically do not provide feedback on behavioral performance until the subject wakes up and is tested. If the interventions are applied more than necessary, it prevents other memories from being consolidated and can even cause deterioration of the memory the intervention is attempting to reinforce. If the interventions are applied less than necessary, the desired behavioral performance will not be achieved.

The present invention allows for a targeted personalized system for enhancing memory in both normal subjects and those with learning difficulties related to memory consolidation. As can be appreciated by those skilled in the art, such an intervention control system could be used for teaching and training (e.g., pilot training, vehicle or machine operation, memorization, etc.), or as a commercial product. It can also be deployed by people or subjects on specific missions. Missions such as surveillance and after-mission debrief require detailed memories that could be enhanced and clarified by the invention. The system can also be used to accelerate mission rehearsal time.

Since there is recent widespread interest into brain enhancement technologies, and there are several commercial systems on the market today, the control technique system of the present invention can be easily incorporated into a variety of existing or new memory intervention products. As a non-limiting example, the model-based predictive controller of the present invention can be utilized with the transcranial current stimulation memory intervention systems (having electrodes) as produced by Neuroelectrics, Soterix Medical, and/or EGI. Neurolectrics is located at 210 Broadway, Suite 201, Cambridge 02139, Mass., USA. Soterix Medical is located at 237 W 35th St, New York, N.Y. 10001, while EGI (or Electrical Geodesics, Inc.) is located at 500 East 4th Ave., Suite 200, Eugene, Oreg. 97401. The controller could also be used with the audio or odor memory interventions used in university laboratories. Additional details for some exemplary intervention systems may be found in U.S. patent application Ser. Nos. 15/227,922 and 15/332,787, which have been incorporated herein by reference.

Products that incorporate the present invention will enable people to reinforce episodic memories and acquire skills faster while they sleep. The present invention, when paired with a memory consolidation or intervention technique, automates the supervision required to apply the technique, and makes it unnecessary to apply the intervention indiscriminately throughout the night. Thus, the present invention is part of the transition to move these techniques out of clinical settings and into home use.

(4) SPECIFIC DETAILS OF VARIOUS EMBODIMENTS

As noted above, this disclosure provides a cognitive model-based predictive controller (or intervention control system) that improves the effectiveness and efficiency of interventions that produce replay of specific memories. The intervention control system incorporates a model of the way the human brain encodes and consolidates memories of events and skills during waking experience and sleep. The model is personalized to simulate a particular individual subject based on biometric data from the subject. There are surely many uses for such a model, but a desired implementation is to use it to predict how well a particular person can recall a specific memory or perform a specific skill at some time in the future. That prediction is then used to control an intervention to improve the memory or skill.

Although similar to the system as disclosed in U.S. Ser. No. 15/682,065, this disclosure provides a different design for the model that in some embodiments has improved speed and/or efficiency. The cognitive model of this disclosure quantitatively simulates the impact of sleep on long-term memory function and teases apart equally important contributions from waking encoding in short-term memory and sleep consolidation in long-term memory. Speed and efficiency can be critically important for interventions like the desired implementation which must make decisions on how to intervene on every positive phase of the slow-wave sleep oscillation (SWO) during the deepest stage of sleep (i.e., non-rapid eye movement (NREM) sleep). There are a limited number of these oscillations during a night of sleeping (SWOs are at a frequency of <1 Hz for often much less than 90 minutes of a night's sleep), and the electroencephalogram EEG analysis of the dynamically changing SWO frequency and recognition of the identity of a replay takes time before the model can simulate the results. Therefore, it is desirable for the model to make behavioral predictions within 100 milliseconds (ms) after a reported memory replay during the average 500 ms time between the positive phases of SWO to control memory interventions during the next positive phase of SWO. Its subject-specific predictive power in the context of task performance comes from simulating non-invasively assessed markers of attention during encoding as well as the duration and quality of consolidation periods. For further understanding, described below is a recap of the basic architecture of the intervention control system (parts of which were originally disclosed in U.S. Ser. No. 15/682,065), followed by a detailed description of the new model as incorporated into the intervention control system.

(4.1) Basic Architecture

Figure 3:
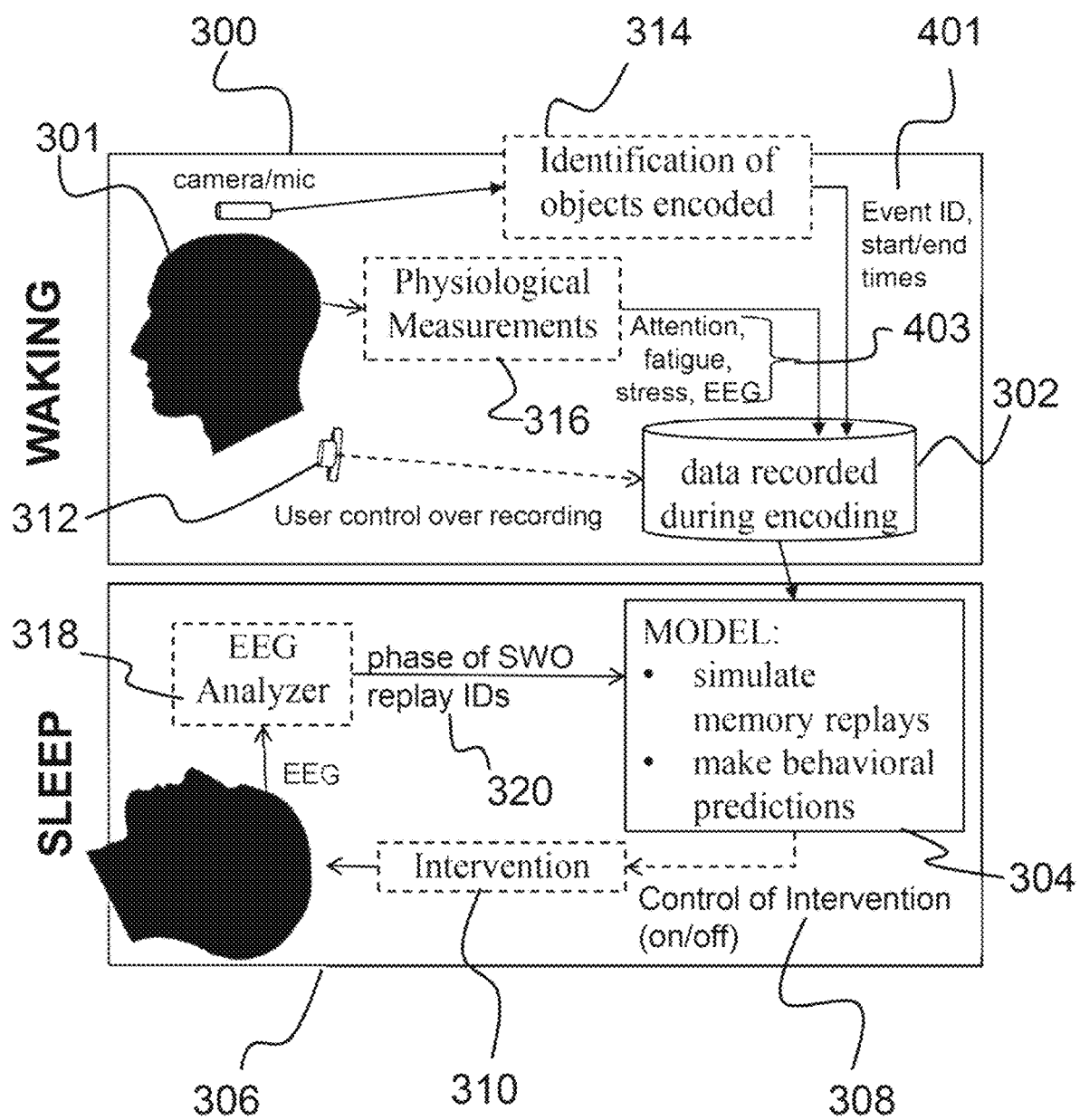
FIG. 3 is an illustration of a closed-loop model-based control system according to some embodiments of the present invention, that simulates behavioral performance and controls when to apply an intervention.

FIG. 3 provides an illustration of the basic architecture of the intervention control system described herein. As shown, during waking hours 300, the control system captures data 302 during waking for model updating. The system then uses a cognitive model 304 to simulate memory consolidation during sleep 306 or quiet waking periods. The model 304 simulates behavioral performance and controls 308 when to apply the intervention 310.

During waking experience 300, when a user 301 is about to experience an event that must be remembered accurately, data recording 302 is initiated either by some automated decision system or by the user 301 (e.g., user controlled activation switch 312), Prior art systems can be used to identify 314 the percepts that are most salient to the subject 301 at that time. For example, for visual items, an eye tracker can be used to decide what the user is looking at; e.g., an image chip is formed around visual fixations averaged over a short (1 sec) time window. Alternatively, the user 301 can actually take a static picture of the item of interest. These images (i.e., either selected by the eye tracker or by the user 301) can be identified using an open-source system, such as ImageNet/GoogleNet, to provide a semantic symbol that identifies the object. For speech recognition, there are many systems known to those skilled in the art that can recognize speech, a non limiting example of which includes the Dragon speech recognition software by Nuance Communications, Inc, located in Burlington, Mass.

A physiological measurement module 316 is included to obtain physiological measurements based on biometric sensor data (e.g., biometric data) from the subject. Any suitable biosensor data or measurements can be obtained. For example, electroencephalography (EEG), electromyography (EMG), and/or electrocardiogram (ECG) measurements can be obtained from the user 301 or subject using the appropriate equipment. Based on analysis of the physiological measurements, a variety of current states (biometrics) of the user 301 can be inferred using any suitable technique known to those skilled in the art. For example, mental fatigue significantly modulates the amplitude of certain event-related potentials (ERPs), and stress can be inferred from electrocardiogram (ECG) read-out of heart rate variability. A small amount of stress can improve encoding strength, but higher levels of stress interfere with encoding. Additionally, attention, or vigilance, can be estimated from EEG and EMG using any suitable method for estimating such biometrics from EEG or ECD or EMG or other biometric sensors, a non-limiting example of which includes the process as described in U.S. Provisional Application No. 62/516,457, filed on Jun. 7, 2017, the entirety of which is hereby incorporated by reference.

At the end of a day in which a memory of a specific event was trained and/or tested, the system can be employed during a sleep phase 306. The system includes an intervention module 310 employed in the sleep phase 306 that associates a cue like an odor, a sound, or electrical stimulation with the memory of interest during waking, and reapplies it during sleep or quiet waking as a cue to trigger a recall of the specific cued memory. The intervention module 310 is any suitable module that applies the aforementioned intervention, non-limiting examples of which include the modules described in Literature Reference Nos. 1 and 2.

The system also includes an EEG Analyzer module 318 that can detect the sleep phase 306 or stage, including detection of Slow Wave Oscillations (SWO) that occur mostly during the deepest stages of sleep (non-rem stage 3 and 4), although they can occur during times of deep restfulness in a quiet waking state as well. For online operation, only a rolling window of the data need be kept, just enough to assess the identity of the last replay (e.g., a 400 ms-1 s temporal window of the positive phase of the last slow wave oscillation).

The EEG Analyzer module 318 is any suitable module that is operable to provide the aforementioned operation. For example, sleep stages are detectable by widely available commercial sleep monitors. The phase of SWO can be ascertained currently by analysis of the EEG signal using any suitable technique known to those skilled in the art, a non-limiting example of which includes the technique described in Literature Reference No. 4. The intervention control system (i.e., controller of the present invention) controls the intervention by turning the intervention on or off based on a prediction of the intervention's effect on the behavioral results. Such predictions are provided by the cognitive model 304, which simulates the replay of memories during sleep, and predicts the behavioral results of such replay. The cognitive memory model 304, subject of the current disclosure, is described in further detail below.

(4.2) Cognitive Model

As noted above and shown in FIG. 4, the intervention control system uses a cognitive model 304 that simulates encoding, decay, consolidation, and recall of novel multi-modal experiences and knowledge in real-world environments. The main sub-modules of the cognitive model 304 are a Short-Term Store (E) 400 and a Long-Term Store (K) 402.

Figure 4:
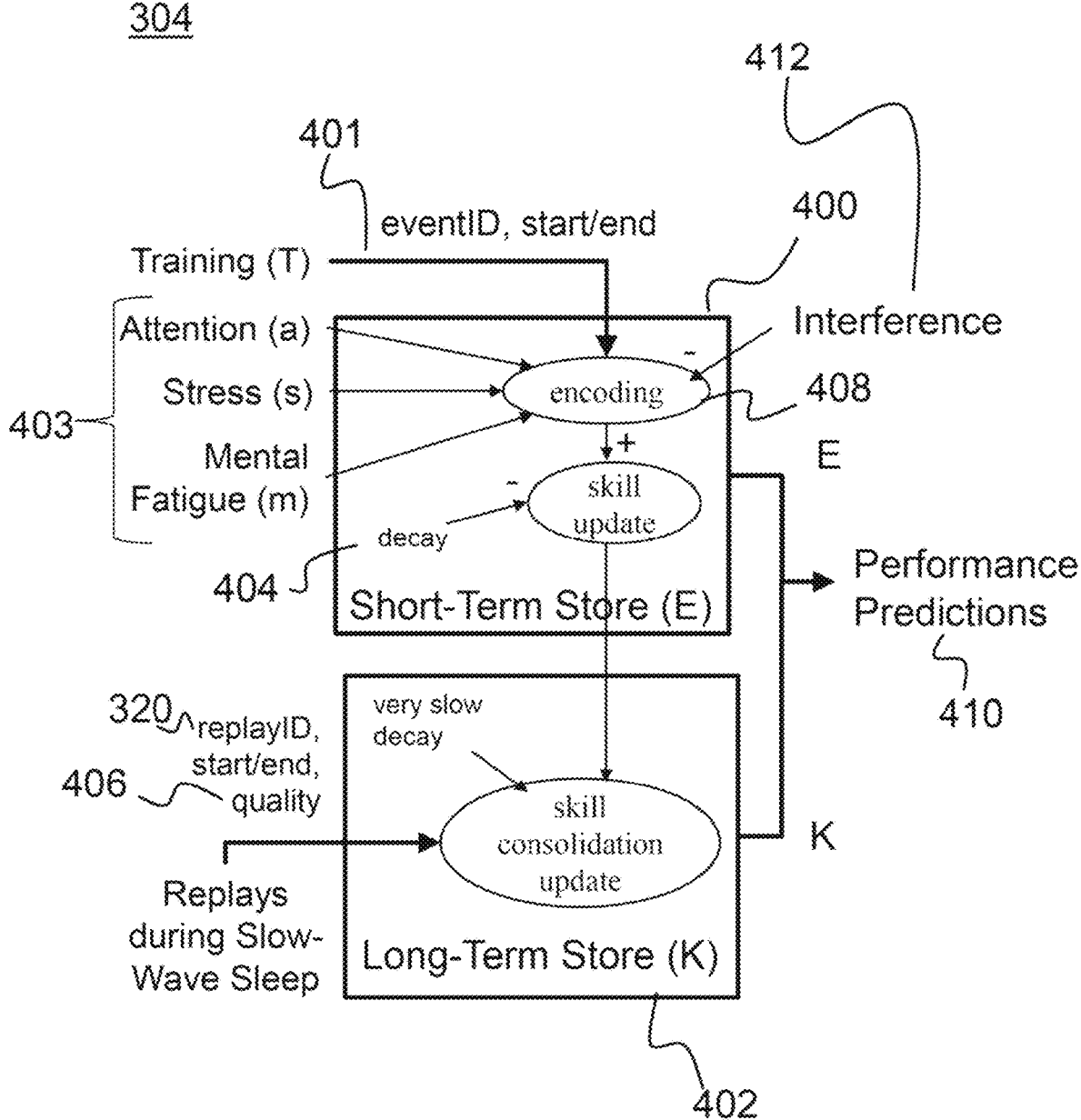
FIG. 4 is an illustration depicting short-term store (E) and long-term store (K) modules as implemented in the closed-loop model-based controller according to some embodiments of the present invention, which are used to simulate encoding, decay, consolidation, and recall of novel multi-modal experiences and knowledge in real-world environments.

The square boxes in FIG. 4 represent modular software components, and the rounded boxes represent software processes with data flowing between them. During waking (depicted as element 300 in FIG. 3), a sensory event is identified with a unique ID and a start and end time and given as a training input (T) 401 to identify each relevant experience (both task related and distractions or interfering experiences). Biometrics 403 (e.g., biometric data) are also provided by the physiological measurements module 316 of FIG. 3, in terms of levels of attention (a), mental fatigue (m), and stress (s) during the training period.

During the sleep phase 306, EEG is analyzed; during the slow-wave sleep stage, each positive phase of the slow wave oscillation (SWO) is when replays happen, and the EEG analyzer 318 provides the IDs 320 of each recognized replay. The cognitive model 304 is not specific to the type of skill being learned and can be easily adapted to a number of tasks. Referring again to FIG. 4, the software processes of encoding 408 and skill update subject to decay 404 are described and quantified in Equations 1 through 3. Further, the skill consolidation update process in FIG. 4 is described in Section 4.4 below and Equation (4).

In the following discussion, the term "skill" is used to describe a memory, possibly associated with actions, such as how to assemble a complex piece of equipment, or what happened during a mission for later debrief. The cognitive model 304 represents the user's ability to recall that skill quickly and easily in terms of the "level" of that skill in both short term (E) and long term (K) memory. The user's interactions with each skill are called training, which could be a formal pedagogical training session with an instructor, or simply experiences in the environment. Each training experience on skill x along with associated biometrics is reported to the Short-Term Store (F) 400, which simulates the training effect on that skill ($E_x$), using the following Equation (1):

$$\text{Training } \frac{dE_x}{dt} = \frac{-E_x}{\tau_E} + \varrho T_x(\text{biometric\_factors}) - \text{distraction\_factor} \quad (1)$$

The distraction_factor is described in Equation (2), and the biometric_factors are described in Equation (3). During training, short-term skill improves based on a training rate (T) personalized to the subject ($\rho=1$). During testing, short-term skill improves at a slower rate as the subject is not receiving feedback on their performance, so $\rho<1$. Biometrics time series 403 measured from the subject such as attention, mental fatigue, and stress modify rate of short-term skill acquisition. Note these relevant variables will be extracted in near real time using brain/body signals from the subject. The biometric_factors modulate the training efficacy ($T_x$) to the extent that the biometrics correlate with performance, as described below in the section on Personalization and Biometric Factors. At all times short-term skill levels decay 404 at a constant exponential rate, $\tau_E$ and increase by a factor $T_x$ that reflects the quality or efficacy of training on skill x. Both of these values must be estimated in advance by performing a pilot test with the subject, training a similar skill in a controlled setting, for a similar length of time, and then measuring performance at several time points afterwards. The subject must not sleep during this test time, since that adds a consolidation factor shown below in Equation (2) that improves performance and would confound the estimate of short-term memory decay. $T_x$ is a skill-specific and subject-dependent learning rate, determined by the slope of the subject behavioral performance data (computed by applying a $1^{st}$ order linear fit). Although other values can be used, the default value for $\tau_E$ in one example is 80,000 to simulate the way short-term memories, which are quickly learned, also quickly decay. In between training periods on a particular skill, including during sleep periods other than slow-wave sleep, the $T_x$ factor is 0, so the skill level simply decays. Thus, $\tau_E$ is the slope of the subject performance data in between training periods that don't include sleep. A testing period provides extra practice to the subject but doesn't have as high a training effect since there is no feedback, so the $T_x$ factor for training is a fraction of its training value proportional to the predicted performance level of the subject since without practice the subject can only practice what they already know. A desired implementation uses $\rho$=0.5 during training, but this value is subject and skill-dependent as well, so it must also be estimated by comparing the subject performance across a training period versus that across a test period. The difference in slope is $\rho$.

Depending on the learning paradigm, it could be useful to make explicit the effect of distraction on learning. As an example, if the skill involves observing a series of events, non-relevant distractions can pull the user's attention away from the relevant events. The distraction_factor is this explicit modulation on the rate of learning. Equation (2) provides the factor in Equation (1) that reduces learning if there is a training effect ($T_x$>0). D is 1 during the time that a distractor is present, causing the distraction to reduce the training effect by a fractional amount $y_d$. The d*interaction factor adds to the distraction an amount d if the user interacts with the distractor in some way; for example, if the gaze is averted from the relevant event to the non-relevant distractor (as measured by a gaze-tracker), this factor can be used. The distraction_factor is as follows in Equation (2):

$$\text{distraction\_factor}=(T_x(x)>0)*(D>0)+d*\text{interaction} \quad (2)$$

(4.3) Personalization and Biometric Factors

The cognitive model 304 is personalized by incorporating biometrics 403 measured by prior art techniques, including measurements of the subject's fatigue, stress, and attention during waking. These inputs are used to modulate the initial activation level of the memories when they are learned or trained (the time of memory encoding). At times other than task-relevant training and testing, biometric parameters identify memory-relevant physiological states and replay parameters that change the model's mode of operation during periods of waking, quiet waking, and the stages of sleep.

Figure 5:
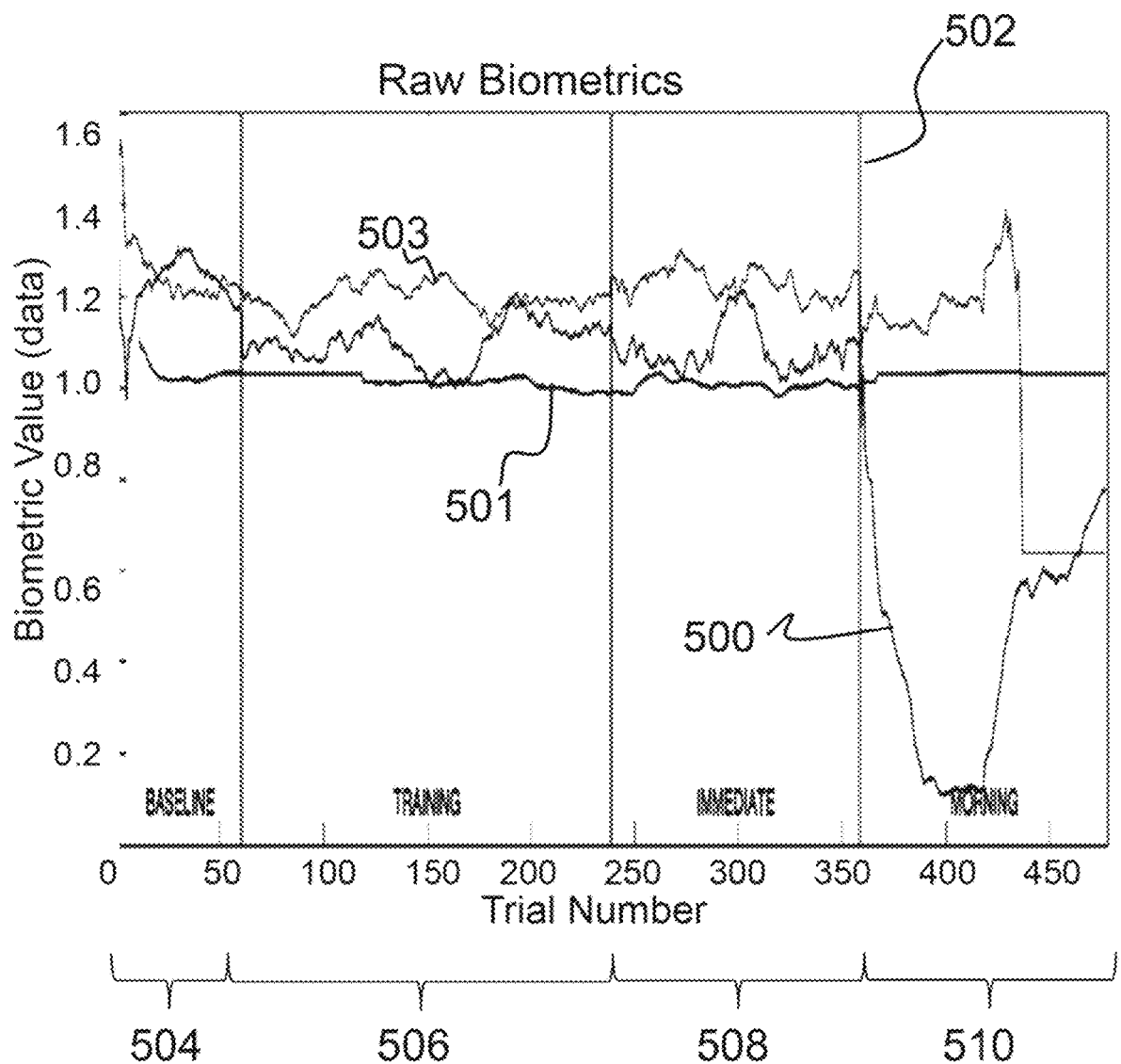
FIG. 5 is a graph illustrating raw biometric values for fatigue, stress, and attention as extracted from EEG from a subject in a pilot task.

Three biometrics are currently extracted from EEG using prior art techniques: mental fatigue, stress, and attention. An example of these raw biometric values (on a (0,2) scale) for a given subject in a pilot task is shown in FIG. 5, showing in particular how mental fatigue 500 is significantly reduced after sleep 502. FIG. 5 also depicts stress 501 and attention 503 across the trials.

The baseline 504 is an acclimation period that, in this example, includes trials 0-60. Task training 506 was trials 61-240, and the immediate test 508 was right after training 506. Biometrics were fairly flat through the first day training and testing (to trial 355), but in the morning 510 tests (trials 356-475 after sleeping) the fatigue 500 metric is significantly lower.

Figure 6:
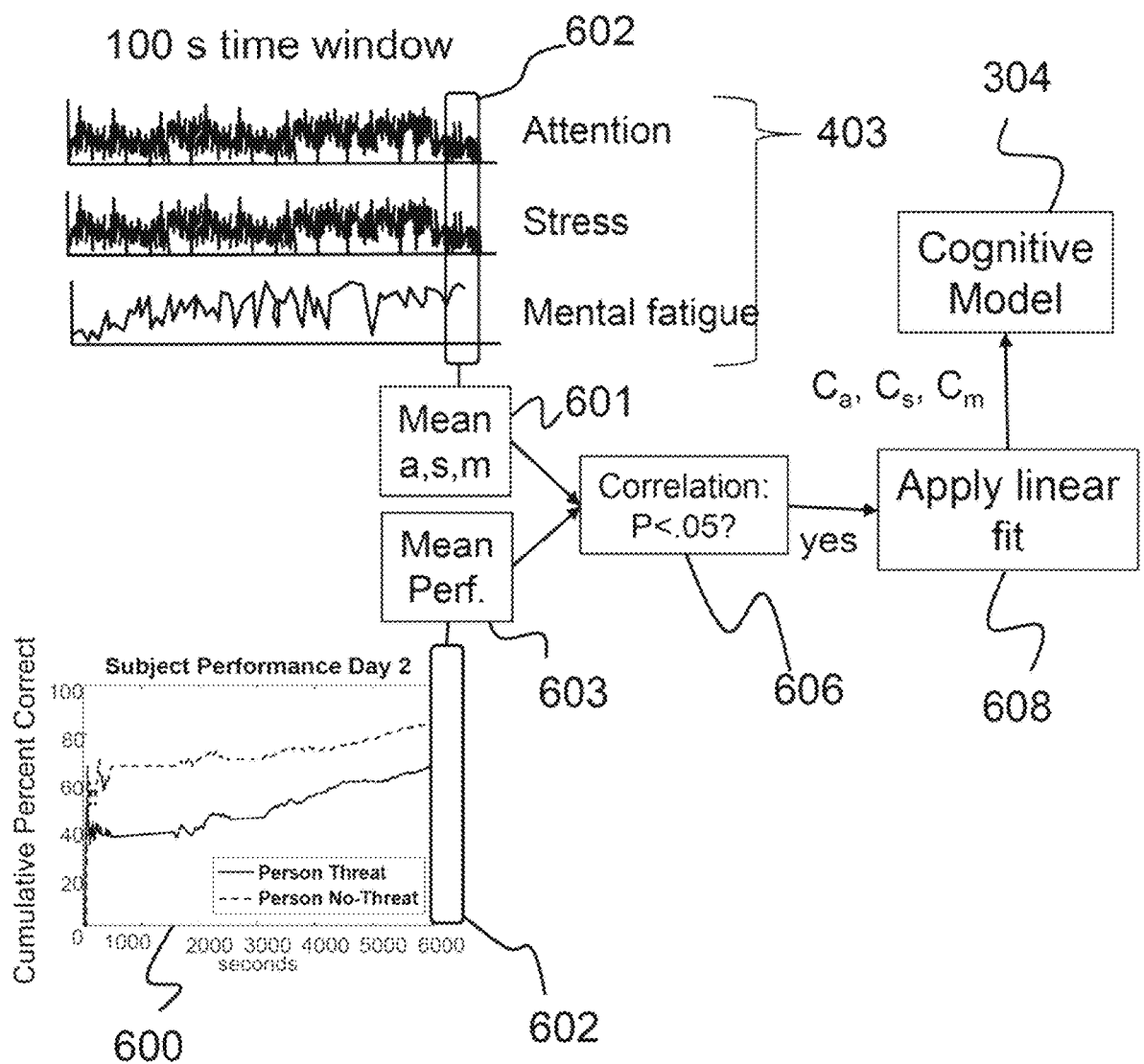
FIG. 6 is an illustration depicting a method of determining modulation parameters for biometric influence on model predictions.

The effect of biometrics on the model simulation is modulated by the amount of correlation between each biometric value and the subject's performance. The online update method, shown in FIG. 6, is based on degree of correlation with performance (using linear fit parameters for significant correlations). Specifically, FIG. 6 illustrates a method of determining modulation parameters for biometric influence on model predictions.

The biometric influence is updated every m trials (currently m=1). A rolling mean 601 and 603 of each biometric 403 and subject behavioral performance metrics 600, respectively, is computed in a temporal window 602 (currently 100 seconds as shown in the figure). Each rolling mean biometric 601 is correlated with each rolling mean performance metric 603, and only incorporated into the cognitive model 304 (via a linear fit 608) for periods when the correlation 606 is significant (i.e., where the p-value is <0.05 (or other predetermined threshold). Equation (3) shows the biometric_factors shown in Equation (1) for the cognitive model's 304 update to the short-term memory level $E_x$.

$$\text{biometric\_factors}=(c_aA+y_a)(c_mM+y_m)(c_sS+y_s) \quad (3)$$

Figure 7:
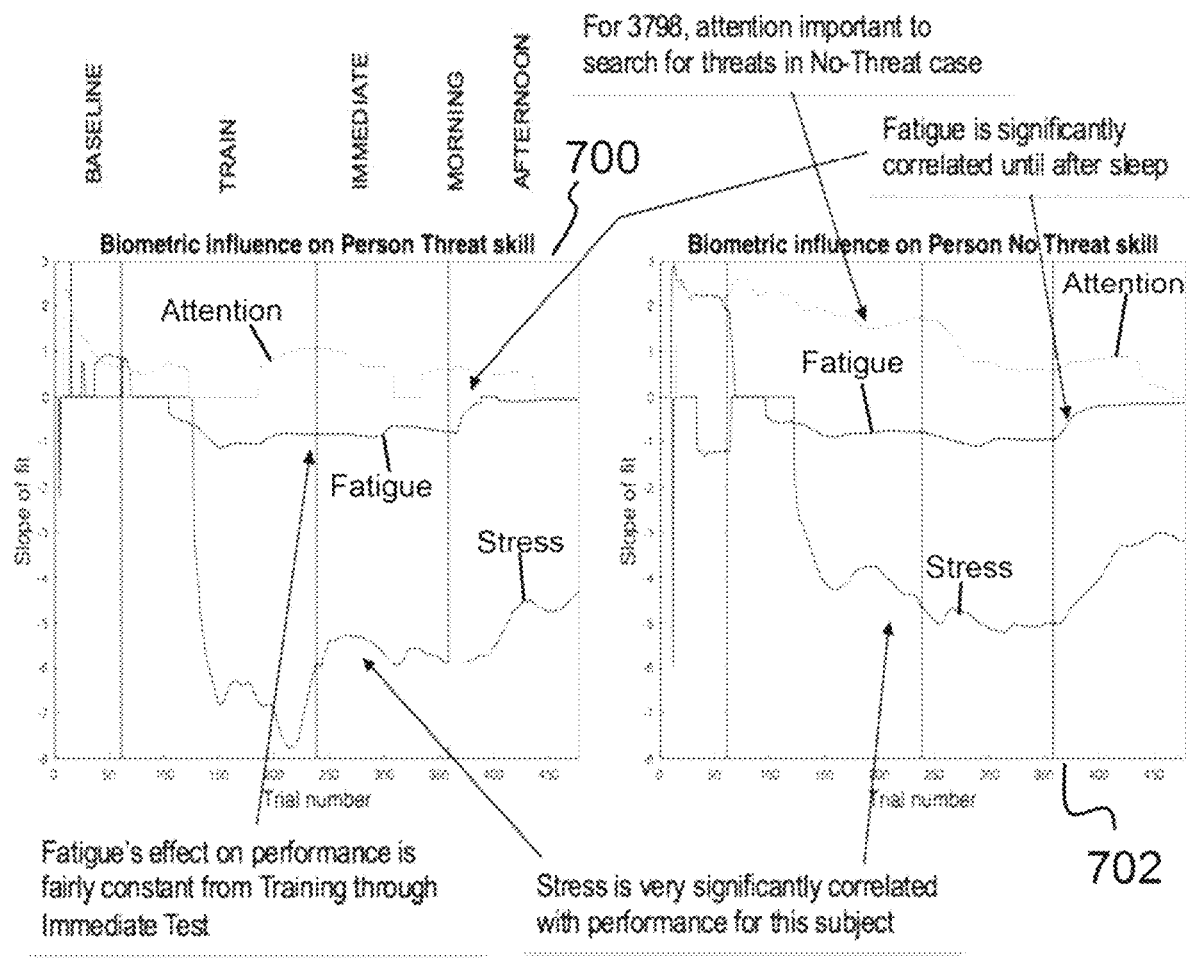
FIG. 7 is an illustration depicting biometric modulation parameters for the subject based on the raw biometric values shown in FIG. 5.

Here A, M, and S are attention factor, mental fatigue factor, and stress factor (each adjusted to −1 to 1 range by subtracting 1), and c is vector of parameters that modulate the impact of the respective biometric. If the correlation for a biometric is not significant, the $c_x$ parameter is set to 0 for that biometric and the corresponding $y_x$ is set to 1. However, if the correlation is significant for a certain time period, a first-order linear fit 608 is used to find a slope and intercept of a regression line that relates the biometric to the performance. For example, a matlab implementation of such a linear fit 608 uses the function polyfit as follows:

coeff=polyfit(biometric_vector, matching_performance_vector, 1);
c=coeff(1);
y=coeff(2);

FIG. 7, for example, shows the slope of the polyfit curve for one subject (referred to as Subject 3798) in the person threat skill 700 and no-threat skill 702 of the task mentioned above. The "threat skill" 700 on the left is the skill of seeing threats in images that show subtle threats. The "no-threat skill" 702 is the skill of identifying safe situations. The vertical black lines in the graphs demarcate the 4 periods or sessions: Baseline, Training, immediate, and Morning. Sleep came between Immediate and Morning. Some notes point out possible explanations.

These fits were based on the raw biometrics shown in FIG. 5. Note that attention has a positive correlation with performance, throughout all 4 sessions, particularly in the no-threat 702 skill, where the subject must search the scene for threats.

(4.4) SWS Replay Simulation

Based on a widely accepted theory backed by experimental data, during sleep memories are "replayed" which is a type reactivation of a short-term memory. As FIG. 3 illustrates, during slow-wave sleep, the EEG Analyzer 318 will sense the sleep stage 306 and the phase of slow-wave oscillations. The model simulates the consolidation benefit of each particular memory that is replayed, which it uses to then predict the ability of the subject to subsequently recall and use that memory. The memory that was replayed is then identified by a "replayID" which is a unique identifier. Determining which replay just occurred requires a machine learning technique that is out of the scope of this invention, but the basic idea is to train a classifier using machine learning on the EEG data of the subject during the time the memory is being encoded (in waking), and then using this classifier on the EEG during sleep to rate the likelihood that certain EEG patterns represent a replay of that memory. So the "replayID" input 320 in FIG. 3 and associated "quality" 406 input in FIG. 4 can take the form of a probability distribution over all possible skills or replayIDs 320, including the possibility that the replay was just background or an unknown memory reactivation. The probability of ReplayID is described below with respect to Equation 5. Short-term memory decays during the night but long-term skill improves whenever a memory is replayed; each memory replay increases consolidation, of the skill that is replayed, according to equation (4).

$$\text{SlowWave Sleep: } \frac{dK_x}{dt} = S * [(E_x - K_x)]^+ \quad (4)$$

S is a sleep consolidation coefficient; S=1 in a desired implementation. Equation (4) says that the increase in the level of skill x in long-term memory ($K_x$) is a function of the difference between the level of the skill in long-term memory vs. that in short-term memory. $[h]^+$ is the Heaviside step function, which is 0 for h<0, or h for h≥0. That is, consolidation of skills means that the long-term memory of the skill x approaches the level in short-term memory. Long term memory is persistent with very slow decay, but short-term memory decays quickly; the Heaviside function prevents K from decaying when the short-term memory E falls below long-term K.

(4.5) Probabilistic ReplayID during Slow-Wave Sleep

ReplayID 320 and a quality measure 406 are shown as an input to the system in FIGS. 3 and 4, and if no replays are input during the night, memory representations in the model's short-term memory would decay without consolidation to long-term memory. The alternative approach to having reliable replay identification is to employ a probabilistic method, where the probability of a memory getting activated is based on the recency, frequency, and strength of encoding (encoding strength) of each memory, and the likely effect of any intervention. The probability can be computed as in Equation (5), as follows:

$$P(\text{replay}_x) = \Sigma_i t_i^{-d} + T_x(c_a A + y_a)(c_m M + y_m(c_s S + y_s)) \quad (5)$$

(4.6) Behavioral Predictions

Memory consolidation occurs during slow-wave oscillations, as measured by EEG, during NREM sleep states, so when such states are sensed and reported to the cognitive model 304, the model 304 simulates the strengthening of individual memories (i.e., association strength representation). Prior art sensing techniques can report the duration and speed of each SWO. Based on the discussion in the previous subsection (SWS Replay simulation), the model 304 chooses which memory to replay in simulation, increasing consolidation (k) for that memory.

During slow-wave sleep, short-term and long-term skill levels are combined to predict final performance. Each time a replay event occurs, or at regular intervals through the SWS duration, the model 304 will make predictions 410 of behavioral performance for the target memory. The behavioral prediction 410 takes the form of a normalized probability of recall; i.e., how likely is the desired recall compared to other memories in STM and LTM. If predicted behavioral performance at a future time of interest is less than the desired level, then the model tells the intervention module 310 to apply the target memory cue in the upcoming SWS UP state. When predicted performance crosses the desired level the model 304 ceases intervention (i.e., causes the intervention module 310 to turn off the intervention). But replay assessment continues, with incorporation of the parameters of any replay event into the model 304. Replays of contradictory information acquired in the recent past prior to target encoding 408, or subsequent to target encoding 408, could impair future task performance related to the memory of interest.

Another aspect is tuning the model 304 to match its performance predictions 410 to empirical behavioral data from the user. Model parameters that can be tuned are time constants for learning and consolidation, and modulation parameters for factors such as fatigue, stress, and attention.

Short-term and long-term skill levels are combined using a logistic function (see Equation 6) to predict final performance (see Equation 7). Interference between skills is computed by a method such as that documented in the subsection below, resulting in an interference matrix $i_{xy}$. The calculation of Performance $P_x$ is depends upon chance (ch=0.5) which is likelihood of a correct response if subject were to respond at random. As $K_x$ and $E_x$, under all normal circumstances, range from 0 to 1, $N_x$ is generally between 0 and 1. A notable exception is when the sum of the interference values is negative and has an absolute value larger than the combined total of E and K. In practice this would correspond to a situation in which the subject has learned something that would cause them to actively avoid the correct answer such as being trained on "If A, respond B" when the correct response was "If A respond C." If $E_x$, $K_x$ and i are 0 $N_x$ will be 0. As the value of $(E_x+K_x+\Sigma i) \to \infty$, $N_x$ approaches 1. When $N_x$=0 indicating that no effective learning has occurred, performance ($P_x$) will be equal to chance. If $N_x$=1 this indicates perfect ability with the skill and $P_x$ will be equal to 1 indicating no errors in response.

$$N_x = \frac{2}{1 + e^{-\left(K_x + E_x + \sum_{y \neq x} i_{xy}(K_y + E_y)\right)}} - 1 \quad (6)$$

$$\text{if } N_x > 0, P_x = N_x(1 - ch) + ch, \quad (7)$$
$$\text{else } P_x = N_x ch + ch$$

(4.7) Interference Between Skills $i_{xy}$ represents the coefficient of interference (depicted as element 412 in FIG. 4) between two skills. A high positive value would indicate that learning skill x is very helpful in performing skill y. If two skills x and y overlap entirely, the subject is expected to make all of the same responses to all test cases for both skills, and $i_{xy}$ would have a value of 1. A high negative value indicates that learning one skill makes performance on the other decline. If two skills indicate completely opposing responses to all relevant test cases, $i_{xy}$ would have a value of −1. For any skills x and y, $i_{xy}$ can either be measured empirically by observing what effect learning skill x has on the performance of skill y, or it can be estimated by measuring the degree of overlap between skills. To estimate the overlap between two skills x and y, assign a value of 1 to each test scenario in which skill x indicates the same response as skill y. Assign a value of −1 to each test scenario in which skill x indicates a conflicting response with skill y. $i_{xy}$ will be the average of these values weighted by the frequency with which each test scenario occurs.

(4.8) Improvement of Predictions Over Time

When model parameters are estimated using each subject's data, the model 304 is better tuned to predict individual trends. This means that as more data becomes available, the model's 304 estimates of $$\frac{dE_x}{dt} \text{ and } \frac{dK_x}{dt}$$

(Equations 3 and 4) improve.

(4.9) Overview of Model Performance

Figure 8A:
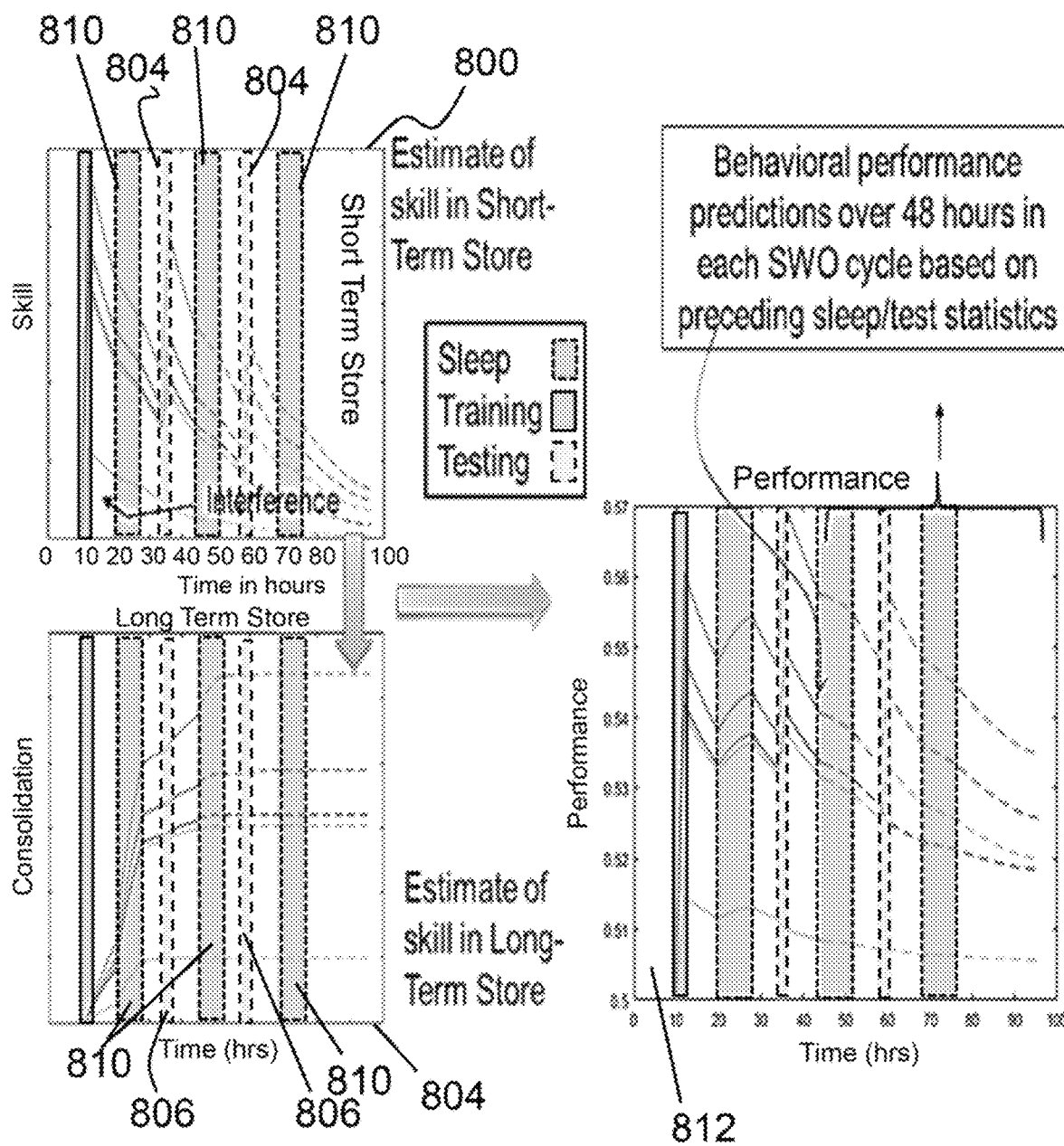
FIG. 8A is an illustration including graphs that depict how model estimates change during training, testing and sleep events, representing the strength of representation in short-term and long-term memory, and how changing short-term representations are combined with the long-term representations to produce the performance predictions over time.
Figure 8B:
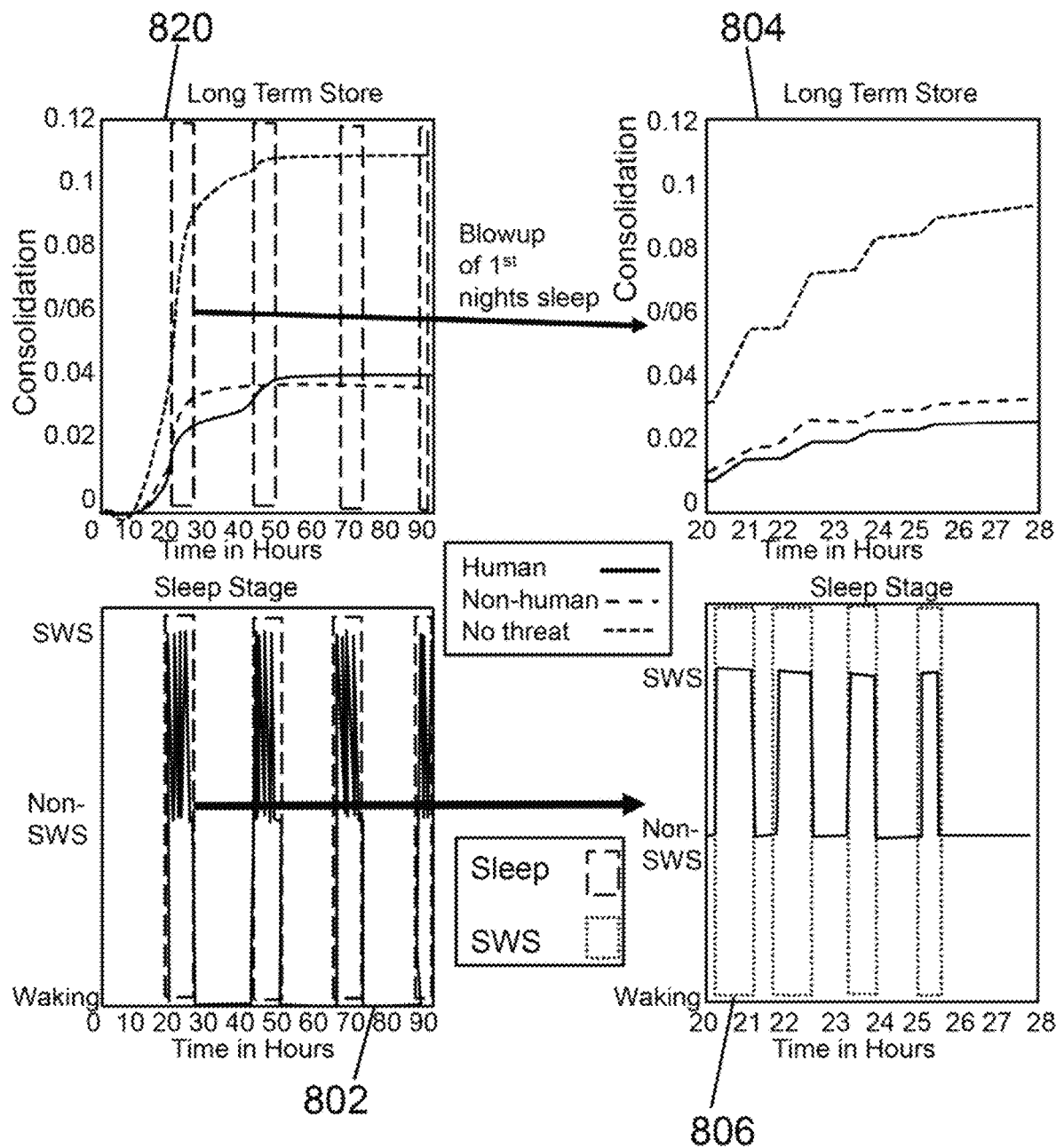
FIG. 8B is an illustration including graphs that depict how the skill representations in the long-term store rise during sleep, during the times when slow-wave oscillations are taking place (SWS periods).

FIGS. 8A and 8B depict a simulation of how the internal model representations of skill level changes during training, testing and sleep events, representing the strength of representation (i.e., association strength representation) in short-term and long-term memory. These representations are produced by Equations 1-7, using stimulus from an actual threat detection training experiment. This experiment was a threat-detection task, with 3 skills: detect human threats, detect non-human threats (e.g., a bomb), and detect when no threat was present. FIG. 8A plots the level of encoding of the 3 skills over a 100 hour period, including 3 nights of sleep. Specifically, FIG. 8A includes charts depicting skill estimate in the short-term store 800 and long-term store 802. Encoding occurs during training 804 and raises the level of skill in the short-term store the training 804 bands in upper left plot); but doesn't affect long-term memory skill 802 levels (bands 806 in lower left plot). Consolidation occurs during slow-wave sleep (bands 810 in all plots), benefitting long-tens memory but not short-term memory representations. The changing short-term representations are combined with the long-term representations to produce the performance predictions over time 812, plotted in the right side of FIG. 8A.

The charts in FIG. 8B focus on the how the skill representations in the long-term store rise during sleep, during the times when slow-wave oscillations are taking place (SWS periods). The upper left plot 820 shows that while all 3 skills benefitted during the night, the no-threat skill had the most replays and the level of that skill gained the most in long-term memory. The plots at the bottom of FIG. 8B show the particular stage of sleep of the subject 822: SWS at top, non-SWS sleep in the middle, and waking at the bottom. Each plot on the right side of FIG. 8B, 804 and 806, is a blow-up of the first night's sleep portion of the respective plot on the left. The subject in this example has had 4 periods of SWS during the night, and the level of long-term skill rises for each skill in proportion to the quantity and quality of replays that occur in each period.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fill within the scope of the present invention.

What is claimed is:

1. A closed-loop intervention control system for memory consolidation in a subject, the system comprising:
   one or more processors and a memory, the memory being a non-transitory computer-readable medium having executable instructions encoded thereon, such that upon execution of the instructions, the one or more processors perform operations of:
      recording biometric data during waking encoding of a first memory, the biometric data simulating a memory change of the first memory and representing at least one of attention, stress, and mental fatigue;
      based on the simulated memory change, predicting behavioral performance for the first memory, the predicted behavioral performance being a probability that the first memory can be recalled on cue;
      controlling operation of the intervention system with respect to the first memory based on the predicted behavioral performance of the first memory determined by the simulation, such that if the predicted behavioral performance is less than a predetermined level, activating electrodes to apply a target memory cue to a subject during a slow wave sleep state of the subject and ceasing activation of the electrodes when the predicted behavioral performance exceeds the predetermined level; and
      correlating the subject's performance of a skill after activation of the electrodes with the biometric data, wherein the correlation between biometric data and the subject's performance of the skill is updated every m trials based on a rolling mean biometric and rolling mean performance metric.

2. The closed-loop intervention control system as set forth in claim 1, wherein the simulated memory change represents an increased level of skill in the first memory due to training and biometric factors.

3. The closed-loop intervention control system as set forth in claim 2, wherein simulating the memory change includes encoding and consolidation of a specific memory.

4. The closed-loop intervention control system as set forth in claim 3, wherein the specific memory is encoded in a short-term memory store and consolidated in a long-term memory store.

5. The closed-loop intervention control system as set forth in claim 4, wherein consolidating the specific memory in the long-term memory store includes strengthening representations of the specific memory.

6. The closed-loop intervention control system as set forth in claim 5, further comprising an operation of identifying replays of the specific memory and determining an associated quality, the quality being a likelihood that the specific memory was activated during a certain time period.

7. The closed-loop intervention control system as set forth in claim 6, wherein the quality is based on recency and frequency of practice of the specific memory.

8. A computer program product for closed-loop intervention for memory consolidation in a subject, the computer program product comprising:
   a non-transitory computer-readable medium having executable instructions encoded thereon, such that upon execution of the instructions by one or more processors, the one or more processors perform operations of:
      recording biometric data during waking encoding of a first memory, the biometric data simulating a memory change of the first memory and representing at least one of attention, stress, and mental fatigue;
      based on the simulated memory change, predicting behavioral performance for the first memory, the predicted behavioral performance being a probability that the first memory can be recalled on cue;
      controlling operation of the intervention system with respect to the first memory based on the predicted behavioral performance of the first memory determined by the simulation, such that if the predicted behavioral performance is less than a predetermined level, activating electrodes to apply a target memory cue to a subject during a slow wave sleep state of the subject and ceasing activation of the electrodes when the predicted behavioral performance exceeds the predetermined level; and correlating the subject's performance of a skill after activation of the electrodes with the biometric data, wherein the correlation between biometric data and the subject's performance of the skill is updated every m trials based on a rolling mean biometric and rolling mean performance metric.

9. The computer program product as set forth in claim 8, wherein the simulated memory change represents an increased level of skill in the first memory due to training and biometric factors.

10. The computer program product as set forth in claim 9, wherein simulating the memory change includes encoding and consolidation of a specific memory.

11. The computer program product as set forth in claim 10, wherein the specific memory is encoded in a short-term memory store and consolidated in a long-term memory store.

12. The computer program product as set forth in claim 11, wherein consolidating the specific memory in the long-term memory store includes strengthening representations of the specific memory.

13. The computer program product as set forth in claim 12, further comprising an operation of identifying replays of the specific memory and determining an associated quality, the quality being a likelihood that the specific memory was activated during a certain time period.

14. The computer program product as set forth in claim 13, wherein the quality is based on recency and frequency of practice of the specific memory.

15. A computer implemented method for a closed-loop intervention for memory consolidation in a subject, the method comprising an act of:

causing one or more processors to execute instructions encoded on a non-transitory computer-readable medium, such that upon execution, the one or more processors perform operations of:

recording biometric data during waking encoding of a first memory, the biometric data simulating a memory change of the first memory and representing at least one of attention, stress, and mental fatigue;

based on the simulated memory change, predicting behavioral performance for the first memory, the predicted behavioral performance being a probability that the first memory can be recalled on cue;

controlling operation of the intervention system with respect to the first memory based on the predicted behavioral performance of the first memory determined by the simulation, such that if the predicted behavioral performance is less than a predetermined level, activating electrodes to apply a target memory cue to a subject during a slow wave sleep state of the subject and ceasing activation of the electrodes when the predicted behavioral performance exceeds the predetermined level; and correlating the subject's performance of a skill after activation of the electrodes with the biometric data, wherein the correlation between biometric data and the subject's performance of the skill is updated every m trials based on a rolling mean biometric and rolling mean performance metric.

16. The computer implemented method as set forth in claim 15, wherein the simulated memory change represents an increased level of skill in the first memory due to training and biometric factors.

17. The computer implemented method as set forth in claim 16, wherein simulating the memory change includes encoding and consolidation of a specific memory.

18. The computer implemented method as set forth in claim 17, wherein the specific memory is encoded in a short-term memory store and consolidated in a long-term memory store.

19. The computer implemented method as set forth in claim 18, wherein consolidating the specific memory in the long-term memory store includes strengthening representations of the specific memory.

20. The computer implemented method as set forth in claim 19, further comprising an operation of identifying replays of the specific memory and determining an associated quality, the quality being a likelihood that the specific memory was activated during a certain time period.

21. The computer implemented method as set forth in claim 20, wherein the quality is based on recency and frequency of practice of the specific memory.

* * * * *